US007695715B2

(12) United States Patent
Hardy et al.

(10) Patent No.: US 7,695,715 B2
(45) Date of Patent: *Apr. 13, 2010

(54) MONOCLONAL ANTIBODIES, ANTIGENS AND DIAGNOSIS AND THERAPY OF MALIGNANT DISEASES

(75) Inventors: Britta Hardy, Tel Aviv (IL); Abraham Novogrodsky, Rehovot (IL)

(73) Assignee: Mor Research Applications Ltd., Petach Tikva (IL)

(*) Notice: Subject to any disclaimer, the term of this patent is extended or adjusted under 35 U.S.C. 154(b) by 795 days.

This patent is subject to a terminal disclaimer.

(21) Appl. No.: 11/315,067

(22) Filed: Dec. 23, 2005

(65) Prior Publication Data

US 2006/0099209 A1  May 11, 2006

Related U.S. Application Data

(60) Division of application No. 09/967,719, filed on Sep. 28, 2001, now abandoned, which is a continuation of application No. PCT/IL99/00518, filed on Sep. 30, 1999.

(30) Foreign Application Priority Data

Mar. 31, 1999 (IL) ..................................... 129299

(51) Int. Cl.
*A61K 39/395* (2006.01)
(52) U.S. Cl. .............. 424/130.1; 424/141.1; 424/144.1; 424/153.1; 424/154.1
(58) Field of Classification Search ........................ None
See application file for complete search history.

(56) References Cited

U.S. PATENT DOCUMENTS

| 5,001,225 | A | * | 3/1991 | Taylor ..................... 530/388.6 |
| 5,571,894 | A | * | 11/1996 | Wels et al. ................ 530/387.3 |
| 5,576,184 | A | | 11/1996 | Better et al. |
| 5,897,862 | A | | 4/1999 | Hardy et al. |
| 2004/0180002 | A1 | * | 9/2004 | Young et al. ................ 424/1.49 |
| 2004/0197328 | A1 | * | 10/2004 | Young et al. ............. 424/141.1 |

FOREIGN PATENT DOCUMENTS

| WO | WO95/20605 | 8/1995 |
| WO | WO03/099196 A2 | 12/2003 |

OTHER PUBLICATIONS

Queen et al. (Proc. Natl. Acad. Sci. 1989, vol. 86, pp. 10029-10033).*
Hardy et al. (Proc. Amer. Assoc. Can. Res. Mar. 26, 1999, p. 513, Ab. #3384).*
Queen et al. (Proc. Natl. Acad. Sci. 1989, vol. 86, pp. 10029-10033).*
Riechmann et al (Nature vol. 332:323-327 1988).*
Stedman's Online Medical Dictionary (http://www.stedmans.com) 2008.*

B. Hardy et al., Immune stimulatory and anti-tumor properties of anti-CD3 and BAT monoclonal antibodies: a comparative study, *Human Antibodies*, 8(2)95-98 (1997).
B. Hardy et al., A lymphocyte-activating monoclonal antibody induces regression of human tumors in severe combined immunodeficient mice, *Proceedings of the National Academy of Sciences of the United States of America*, 94(11)5756-5760 (1997).
B. Hardy et al., Activation of human lymphocytes by a monoclonal antibody to B lymphoblastoid cells: molecular mass and distribution of binding protein,*Cancer Immunotherapy*, 40(6)376-382 (1995).
B. Hardy et al.,A monoclonal antibody against a human B lymphoblastoid cell line induces tumor regressionin mice, *Cancer Research*, 54(22)5793-5796 (1994).
S Deyev, Allelic variants of rearranged immunoglobulin heavy and light chain genes in hybridoma PTF-02 and parent myeloma, *Genetica*, 85:45(1991).
Chromcynski et al., Single-step method of RNA isolation by acid guanidinium thiocyanate-phenol-chloroform extraction, *Anal. Biochem.*, 162:156 (1987).
P. Hamlyn et al., Complete sequence of an immunoglobulin mRNA using specific priming and the dideoxynucleotide method of RNA sequencing, 9:4485 (1981).
G. Kohler et al., Continuous cultures of fused cells secreting antibody of predefined specificity, *Nature*, 256:495-497 (1975).
Ig light chain V-region [Mus musculus], Blast search, Accession AAA03012, Queen, C. et al; A humanized antibody that binds to the interlukin 2 receptor, *Proc. Natl. Acad. Sci. USA*, 86(24)10029-10033 (1989).
Immunoglobulin gamma-3-kappa chain V-J and C region precursor [Mus musculus], Accession BAA03483, Takahashi, S. et al., Cloning and cDNA sequence analysis of nephritogenic monoclonal antibodies derived from an MRL/lpr lupus mouse, *Mol. Immunol.* 30(2)177-182 (1993).
Immunoglobulin heavy chain V-region, Accession AAA40564, Lui et al. Purification crystallization and structure of an Fab fragment the neutralizes Human Rhinovirus 14 1993.
Ig kappa chain precursor V (4C11)-mouse (fragment), Accession PL0013, Cheng et al: Structural basis of stimulatory anti-idiotypic antibodies, *Mol. Immunol.*, 25(1)33-40 (1988).
Imunoglobulin heavy chain, Accession CA37412, Li, Y. W. et al: Construction, expression and characterization of a murine/human chimeric antibody with specificity for hepatitis B surface antigen, *Mol. Immunol.*, 27(3)303-311 (1990).

(Continued)

*Primary Examiner*—Peter J Reddig
(74) *Attorney, Agent, or Firm*—Browdy and Neimark, PLLC

(57) ABSTRACT

The invention concerns novel DNA and amino acid sequences of monoclonal antibodies (mAbs) raised against lymphoblastoid cells and peptides to which the mAbs bind to. The invention also concerns diagnostic assays using said antibodies or peptides for detecting individuals with a high probability of having a malignant disease and, at times, for detecting an individual having a specific malignant disease. The invention further concerns pharmaceutical compositions comprising the mAbs or peptides of the invention for use in the treatment of various malignant diseases as well as methods for the treatment of malignant diseases using the mAbs or peptides of the invention.

6 Claims, 26 Drawing Sheets

Monoclonal antibody heavy chain, Accession AAC04532,, O'Connor, K.C. et al.: Anti-DNA antibodies of normal mice immunized with poly (dC) are structurally similar to natural autoantibodies, Feb. 2, 1998.

Immunoglobulin heavy chain, Accession AAA38444, Heinrich, G. et al: Characterization of human T cell-specific chimeric antibody (CD7) with human constant and mouse variable regions, *J. Immunol.*, 143:3589-3597 (1989).

Johnstone and Thorpe, Immunochemistry in Practice, Blackwell Scientific Publications, Oxford, 49-50 (1987).

Reichmann et al.,*Nature*, 332:323-327 (1988).

* cited by examiner

Fig 1

TACTAGTCGACACATGGGCTTTGGGTGTGTGGACCTTGCTCTATTCCTGATGGCAGCTGCCCAAAGTATCCAAGCACA
ATGATCAGCTGTACCGAACCCACACCTGGAAACGATAAGGACTACCGTCGACGGGTTTCATAGGTTCGTGT
            M  A  W  V  W  T  L  L  F  L  M  A  A  A  Q  S  I  Q  A  Q

GATCCAGTTGGTGCTGCAGTCTGGAGACCTGAGTTGAAGAAGCCTGGAGAGACAGTCAAGATCTCCTGCAAGGCT
CTAGGTCAACCACGTCAGACGTCAGACCTCTGGACTCAACTTCTTCGGACCTCTCTGTCAGTTCTAGAGACGTTCCGA
 I  Q  L  V  Q  S  G  P  E  L  K  K  P  G  E  T  V  K  I  S  C  K  A

TCTGGATATACTTTCACAAACTATGGAATGAACTGGGTGAAGCAGGCTCCAGGAAAGGGTTTAAAGTGGA
AGACCTATATGAAAGTGTTTGATACCTTACTTGACCCACTTCGTCCGAGGTCCTTTCCCAAATTTCACCT
 S  G  Y  T  F  T  N  Y  G  M  N  W  V  K  Q  A  P  G  K  G  L  K  W

TGGGCTGGATAAACACCGACAGTGGAGAGTCAACATATGCTGAAGAGTTCAAGGACGGTTTGCCTTCTC
ACCCGACCTATTGTGGCTGTCACCTCTCAGTTGTATACGACTTCTCAAGTTCCCTGCCAAACGGAAGAG
 M  G  W  I  N  T  D  S  G  E  S  T  Y  A  E  E  F  K  G  R  F  A  F  S

TTTGGAAACCTCTCGCCAACACTGCCTATTTGCAGATCAACAACCTCAACAATGAGGACACGCCTACATAT
AAACCTTTGGAGAGCGGTTGTGACGGATAAACGTCTAGTTGTTGGAGTTGTTACTCCTGTGCGGATGTATA
 L  E  T  S  A  N  T  A  Y  L  Q  I  N  N  L  N  N  E  D  T  A  T  Y

TTCTGTGTGAGAGTCGGCTACGATGCTTTGGACTACTGGGGTCAAGGAACCTCAGTCACCGTCTCCTCAA
AAGACACACTCTCAGCCGATGCTACGAAACCTGATGACCCCAGTTCCTGGAGTCAGTGGCAGAGGAGTT
 F  C  V  R  V  G  Y  D  A  L  D  Y  W  G  Q  G  T  S  V  T  V  S  S

CTACAACAACAGCCCCATCTGTCTATCCCTTCCCGGGTTCCA
GATGTTGTTGTCGGGGTAGACAGATAGGGAAGGGCCCAAGGT

Fig 2

```
ACTAGTCGACATGGATTTACAGGTGCAGATTATCAGTTCCTGCTAATCAGTGCCTCAGTCATAATGTCC
TGATCAGCTGTACCTAAATGTCCACGTCTAATAGTCGAAGGACGATTAGTCACGGAGTCAGTATTACAGG
              M  D  L  Q  V  Q  I  I  S  F  L  L  I  S  A  S  V  I  M  S

AGAGGACAAATTGTCCTCACCCAGTCTCCAGCAATCATGTCTGCATCTCCAGGGGAGAAGGTCACCATAA
TCTCCTGTTTAACAGGAGTGGGTCAGAGGTCGTTAGTACAGACGTAGAGGTCCCCTCTTCCAGTGGTATT
 R  G  Q  I  V  L  T  Q  S  P  A  I  M  S  A  S  P  G  E  K  V  T  I

CCTGCAGTGCCAGGTCAAGTGTAAGTTACATGCACTGGTTCCAGCAGAAGCCAGGCACTTCTCCCAAACT
GGACGTCACGGTCCAGTTCACATTCAATGTACGTGACCAAGGTCGTCTTCGGTCCGTGAAGAGGGTTTGA
 T  C  S  A  R  S  S  V  S  Y  M  H  W  F  Q  Q  K  P  G  T  S  P  K  L

CTGGATTTATAGGACATCCAACCTGGCTTCTGGAGTCCCTGCTCGCTTCAGTGGCAGTGGATCTGGGACC
GACCTAAATATCCTGTAGGTTGGACCGAAGACCTCAGGGACGAGCGAAGTCACCGTCACCTAGACCCTGG
 W  I  Y  R  T  S  N  L  A  S  G  V  P  A  R  F  S  G  S  G  S  G  T

TCTTACTGTCTCACAATCAGCCGAATGGAGGCTGAAGATGCTGCCACTTATTACTGCCAGCAAAGGAGTA
AGAATGACAGAGTGTTAGTCGGCTTACCTCCGACTTCTACGACGGTGAATAATGACGGTCGTTTCCTCAT
 S  Y  C  L  T  I  S  R  M  E  A  E  D  A  A  T  Y  Y  C  Q  Q  R  S

GTTTCCCCACTCACGTTCGGCTCGGGGACAAAGTTGGAAATAAAACGGGCTGATGCTGCACCAACTGTATC
CAAAGGGGTGAGTGCAAGCCGAGCCCCTGTTTCAACCTTTATTTTGCCCGACTACGACGGTTGACATAG
 S  F  P  L  T  F  G  S  G  T  K  L  E  I  K

CATCTTCCCACCATCCAAGATCT
GTAGAAGGGTGGTAGGTTCTAGA
```

Fig. 3

```
BAT:    QIQLVQSGPELKKPGETVKISCKASGYTFTNYGMN-WVKQAPGKGLKWMG
VMS2:   ..................................................

BAT:    WINT-DSGESTYAEEFKGRFAFSLETSANTAYLQINNLNNEDTATYFCVR
VMS2A:  .....NT..P..................S.........K.........A.

BAT:    VGYDA----------LDYWGQGTSVTVSS
VMS2:   R..YYGSR.....YGAM............
```

Residue H 53 (Kabat)

BAT: Asp(D)  Germline: Asn(N)

| Mouse V$_H$Misc. | | All Mouse V$_H$ | |
|---|---|---|---|
| Residue | % Frequency | Residue | % Frequency |
| Ile | 43.33 | Gly | 27.60 |
| Pro | 25.00 | Asn | 25.98 |
| Thr | 20.00 | Tyr | 13.72 |
| Leu | 6.67 | Ser | 11.02 |
| Ser | 1.67 | Ala | 7.33 |
| His | 1.67 | Asp | 4.93 |
| Val | 1.67 | Trp | 2.06 |
|  |  | Arg | 1.84 |
|  |  | His | 1.63 |
|  |  | Glu | 1.50 |
|  |  | Thr | 0.73 |
|  |  | Phe | 0.47 |
|  |  | Lys | 0.43 |
|  |  | Val | 0.26 |
|  |  | Leu | 0.17 |
|  |  | Pro | 0.13 |
|  |  | Ile | 0.09 |
|  |  | Gln | 0.09 |
|  |  | Cys | 0.04 |

Fig 3 cont.

Residue H 54 (Kabat)

BAT: Ser(S)  Germline: Thr(T)

| Mouse V$_H$Misc. Residue | % Frequency | All Mouse V$_H$ Residue | % Frequency |
|---|---|---|---|
| Tyr | 30.51 | Asn | 28.79 |
| Asn | 25.42 | Ser | 26.18 |
| Thr | 23.73 | Gly | 22.72 |
| His | 5.08 | Asp | 13.70 |
| Ser | 5.08 | Thr | 3.94 |
| Lys | 3.39 | Lys | 1.63 |
| Asp | 3.39 | Tyr | 1.34 |
| Leu | 1.69 | Ile | 0.38 |
| Ala | 1.69 | Arg | 0.29 |
|  |  | Ala | 0.25 |
|  |  | His | 0.25 |
|  |  | Pro | 0.17 |
|  |  | Phe | 0.13 |
|  |  | Trp | 0.08 |
|  |  | Cys | 0.08 |
|  |  | Val | 0.04 |
|  |  | Leu | 0.04 |

Residue H 57 (Kabat)

BAT: Ser(S)  Germline: Pro(P)

| Mouse V$_H$Misc. Residue | % Frequency | All Mouse V$_H$ Residue | % Frequency |
|---|---|---|---|
| Pro | 100.00 | Thr | 77.80 |
|  |  | Ile | 11.89 |
|  |  | Pro | 2.49 |
|  |  | Ser | 2.11 |
|  |  | Lys | 1.91 |
|  |  | Asn | 1.62 |
|  |  | Ala | 0.87 |
|  |  | Leu | 0.41 |
|  |  | Val | 0.17 |
|  |  | His | 0.17 |
|  |  | Arg | 0.12 |
|  |  | Gln | 0.08 |
|  |  | Met | 0.08 |
|  |  | Phe | 0.08 |
|  |  | Gly | 0.08 |
|  |  | Tyr | 0.04 |
|  |  | Cys | 0.04 |
|  |  | Asp | 0.04 |

Fig 3 cont. (2)

Residue H 76 (Kabat)

BAT: Asn(N)   Germline: Ser(S)

Mouse V$_H$ Misc.

| Residue | % Frequency |
|---|---|
| Ser | 58.33 |
| Asn | 38.33 |
| Ile | 1.67 |
| Tyr | 1.67 |

All Mouse V$_H$

| Residue | % Frequency |
|---|---|
| Ser | 66.26 |
| Asn | 29.73 |
| Thr | 1.42 |
| Arg | 0.90 |
| Lys | 0.34 |
| Asp | 0.34 |
| Gly | 0.26 |
| Ile | 0.22 |
| Tyr | 0.17 |
| Ala | 0.13 |
| Gln | 0.09 |
| His | 0.09 |
| Glu | 0.04 |

Residue H 83 (Kabat)

BAT: Asn(N)   Germline: Lys(K)

Mouse V$_H$ Misc.

| Residue | % Frequency |
|---|---|
| Arg | 51.67 |
| Lys | 35.00 |
| Thr | 8.33 |
| Gln | 1.67 |
| Ser | 1.67 |
| Asn | 1.67 |

All Mouse V$_H$

| Residue | % Frequency |
|---|---|
| Thr | 60.98 |
| Arg | 18.32 |
| Lys | 8.69 |
| Gln | 8.69 |
| Asp | 1.77 |
| Ala | 0.91 |
| Ser | 0.35 |
| Asn | 0.13 |
| Ile | 0.09 |
| His | 0.04 |
| Glu | 0.04 |

Fig 3 cont. (3)

Residue H 93 (Kabat), Vernier Residue

BAT: Val(V)  Germline: Ala(A)

Mouse V_HMisc.

| Residue | % Frequency |
|---------|-------------|
| Ala | 62.71 |
| Met | 25.42 |
| Thr | 3.39 |
| Val | 3.39 |
| Lys | 1.69 |
| Leu | 1.69 |
| Asn | 1.69 |

All Mouse V_H

| Residue | % Frequency |
|---------|-------------|
| Ala | 83.26 |
| Thr | 8.03 |
| Val | 3.74 |
| Ser | 1.36 |
| Gly | 1.27 |
| Met | 0.89 |
| Asn | 0.34 |
| Pro | 0.26 |
| Lys | 0.21 |
| Trp | 0.17 |
| Asp | 0.13 |
| Ile | 0.13 |
| Leu | 0.08 |
| Tyr | 0.04 |
| Phe | 0.04 |
| His | 0.04 |

Residue H 95 (Kabat)
BAT: Val(V)  Germline: Arg(R)

Mouse V_HMisc.

| Residue | % Frequency |
|---------|-------------|
| Tyr | 25.42 |
| Asp | 13.56 |
| Trp | 11.86 |
| Ser | 10.17 |
| Arg | 10.17 |
| Gly | 6.78 |
| Pro | 5.08 |
| Gln | 5.08 |
| His | 5.08 |
| Lys | 3.39 |
| Cys | 1.69 |
| Phe | 1.69 |

All Mouse V_H

| Residue | % Frequency |
|---------|-------------|
| Ser | 16.24 |
| Tyr | 15.18 |
| Gly | 13.81 |
| Asp | 13.28 |
| Arg | 9.00 |
| Glu | 4.41 |
| Asn | 4.37 |
| Leu | 3.53 |
| Pro | 2.96 |
| His | 2.47 |
| Ala | 2.43 |
| Trp | 2.38 |
| Thr | 1.94 |
| Lys | 1.68 |
| Gln | 1.50 |
| Val | 1.15 |
| Ile | 1.15 |
| Phe | 1.10 |
| Cys | 1.06 |
| Met | 0.35 |

Fig 3 cont. (4)

Residue H 98 (Kabat)

BAT: Asp(D)  Germline: Tyr(Y)

| Mouse $V_H$Misc. | | All Mouse $V_H$ | |
|---|---|---|---|
| Residue | % Frequency | Residue | % Frequency |
| Tyr | 56.00 | Tyr | 32.11 |
| Gly | 10.00 | Gly | 24.52 |
| Thr | 6.00 | Asp | 6.79 |
| Ala | 6.00 | Ser | 6.16 |
| Asn | 4.00 | Arg | 4.51 |
| Ser | 4.00 | Asn | 4.41 |
| Asp | 4.00 | Thr | 3.61 |
| Leu | 2.00 | Leu | 3.61 |
| Arg | 2.00 | Ala | 2.18 |
| Pro | 2.00 | Phe | 2.07 |
| Ile | 2.00 | Val | 1.70 |
| Lys | 2.00 | Trp | 1.65 |
| | | Pro | 1.59 |
| | | Ile | 1.22 |
| | | Lys | 1.06 |
| | | His | 1.01 |
| | | Glu | 0.80 |
| | | Gln | 0.69 |
| | | Met | 0.21 |

Fig 3 cont. (5)

Residue H 99 (Kabat)

BAT: Ala(A)   Germline: Tyr(Y)

| Mouse V_H Misc. | | All Mouse V_H | |
|---|---|---|---|
| Residue | % Frequency | Residue | % Frequency |
| Trp | 28.26 | Gly | 27.95 |
| Gly | 15.22 | Tyr | 16.87 |
| Ser | 15.22 | Ser | 16.76 |
| Tyr | 13.04 | Arg | 6.63 |
| Pro | 6.52 | Asp | 4.20 |
| Met | 4.35 | Asn | 4.03 |
| Arg | 4.35 | Thr | 3.73 |
| Asn | 4.35 | Ala | 3.20 |
| Asp | 2.17 | Leu | 3.02 |
| Phe | 2.17 | Pro | 2.78 |
| His | 2.17 | Phe | 2.61 |
| Ala | 2.17 | Val | 2.25 |
|  |  | Glu | 1.24 |
|  |  | His | 0.89 |
|  |  | Lys | 0.89 |
|  |  | Gln | 0.83 |
|  |  | Ile | 0.83 |
|  |  | Met | 0.53 |
|  |  | Trp | 0.53 |
|  |  | Cys | 0.18 |
|  |  | Other | 0.06 |

Residue H100K (Kabat)

BAT: Leu(L)   Germline: Met(M)

| Mouse V_H Misc. | | All Mouse V_H | |
|---|---|---|---|
| Residue | % Frequency | Residue | % Frequency |
| Gln | 61.54 | Phe | 70.91 |
| Thr | 25.00 | Met | 24.40 |
| Ala | 13.46 | Leu | 2.46 |
|  |  | Ile | 0.59 |
|  |  | Val | 0.53 |
|  |  | Ser | 0.41 |
|  |  | Tyr | 0.35 |
|  |  | Thr | 0.18 |
|  |  | Ala | 0.06 |
|  |  | His | 0.06 |
|  |  | Gly | 0.06 |

Fig 4

```
BAT: QIVLTQSPAIMSASPGEKVTITCSARS-------SVSYMHWFQQKPGTSPKLWIY
H4:  ....................S...S............Y.Y.....S...P...

BAT: RTSNLASGVPARFSGSGSGTSYCLTISRMEAEDAATYYCQQRSSFP-----PLT
H4:  ....................S....S.............YH.Y.......-F.

BAT: FGSGTKLEI-K
H4:  ...........
```

Residue L 22 (Kabat)

BAT: Thr(T)  Germline: Ser(S)

| Mouse V$_x$Misc. | | All Mouse V$_x$ | |
|---|---|---|---|
| Residue | % Frequency | Residue | % Frequency |
| Thr | 98.09 | Ser | 50.26 |
| Ser | 1.27 | Thr | 46.44 |
| Ile | 0.64 | Asn | 1.16 |
| | | Arg | 0.71 |
| | | Phe | 0.32 |
| | | Pro | 0.26 |
| | | Ala | 0.26 |
| | | Tyr | 0.19 |
| | | Ile | 0.19 |
| | | Cys | 0.13 |
| | | Other | 0.06 |

Fig 4 cont.

Residue L 26 (Kabat)

<u>BAT: Arg(R)</u> *Germline: Ser(S)*

Mouse V$_x$VI

| Residue | % Frequency |
|---|---|
| *Ser* | 96.79 |
| <u>Arg</u> | <u>1.92</u> |
| <u>Ile</u> | <u>0.64</u> |
| Thr | 0.64 |

All Mouse V$_x$

| Residue | % Frequency |
|---|---|
| Ser | 96.09 |
| Asn | 1.41 |
| <u>Thr</u> | <u>1.28</u> |
| <u>Arg</u> | <u>0.64</u> |
| Ile | 0.32 |
| Cys | 0.06 |
| Met | 0.06 |
| Leu | 0.06 |
| Gly | 0.06 |

Residue L 34 (Kabat)

<u>BAT: His(H)</u> *Germline: Tyr(Y)*

Mouse V$_x$VI

| Residue | % Frequency |
|---|---|
| *Tyr* | 85.62 |
| Phe | 13.73 |
| <u>His</u> | <u>0.65</u> |

All Mouse V$_x$

| Residue | % Frequency |
|---|---|
| <u>His</u> | <u>35.78</u> |
| Asn | 20.49 |
| Ala | 18.73 |
| *Tyr* | 7.89 |
| Glu | 6.14 |
| Ser | 5.20 |
| Gln | 2.00 |
| Thr | 1.57 |
| Val | 0.38 |
| Phe | 0.38 |
| Asp | 0.38 |
| Gly | 0.38 |
| Ile | 0.25 |
| Cys | 0.13 |
| Arg | 0.13 |
| Trp | 0.06 |
| Leu | 0.06 |
| Lys | 0.06 |

Fig 4 cont. (2)

Residue L 36 (Kabat), Vernier Residue

<u>BAT: Phe(F)</u> *Germline: Tyr(Y)*

Mouse V<sub>x</sub>VI

| Residue | % Frequency |
|---|---|
| Gln | 98.76 |
| His | 1.24 |

All Mouse V<sub>x</sub>

| Residue | % Frequency |
|---|---|
| Tyr | *82.43* |
| Phe | <u>11.13</u> |
| Leu | 4.44 |
| His | 0.88 |
| Asn | 0.38 |
| Ser | 0.19 |
| Cys | 0.13 |
| Val | 0.13 |
| Asp | 0.06 |
| Ala | 0.06 |
| Trp | 0.06 |
| Ile | 0.06 |
| Other | 0.06 |

Residue L 42 (Kabat)

<u>BAT: Thr(T)</u> *Germline: Ser(S)*

Mouse V<sub>x</sub>VI

| Residue | % Frequency |
|---|---|
| Pro | 100.00 |

All Mouse V<sub>x</sub>

| Residue | % Frequency |
|---|---|
| Gln | 44.92 |
| <u>Thr</u> | <u>18.73</u> |
| Lys | 10.28 |
| Gly | 9.90 |
| *Ser* | *7.83* |
| Glu | 2.44 |
| Ala | 1.88 |
| Phe | 1.75 |
| Asn | 1.13 |
| Arg | 0.63 |
| His | 0.19 |
| Trp | 0.06 |
| Val | 0.06 |
| Pro | 0.06 |
| Ile | 0.06 |
| Other | 0.06 |

Fig 4 cont. (3)

| | | | |
|---|---|---|---|
| Val | 1.27 | Arg | 19.36 |
| | | Pro | 4.53 |
| | | Thr | 2.94 |
| | | Ala | 1.23 |
| | | Val | 0.92 |
| | | Ile | 0.55 |
| | | Phe | 0.43 |
| | | Gly | 0.37 |
| | | Ser | 0.25 |
| | | His | 0.12 |
| | | Gln | 0.06 |
| | | Asp | 0.06 |
| | | Met | 0.06 |
| | | Lys | 0.06 |

Residue L 72 (Kabat)

BAT: Cys (C)   Germline: Ser(S)

| Mouse $V_x$VI | | All Mouse $V_x$ | |
|---|---|---|---|
| Residue | % Frequency | Residue | % Frequency |
| Ser | 96.89 | Ser | 50.52 |
| Thr | 3.11 | Thr | 47.44 |
| | | Val | 0.56 |
| | | Ala | 0.37 |
| | | Pro | 0.31 |
| | | Ile | 0.31 |
| | | Phe | 0.19 |
| | | Arg | 0.12 |
| | | Tyr | 0.12 |
| | | Lys | 0.06 |

Fig 4 cont. (4)

Residue L 77 (Kabat)

BAT: Arg(R)  Germline: Ser(S)

| Mouse V$_x$VI | | All Mouse V$_x$ | |
|---|---|---|---|
| Residue | % Frequency | Residue | % Frequency |
| Ser | 83.33 | Ser | 48.12 |
| Arg | 10.36 | Arg | 23.28 |
| Thr | 3.85 | Asn | 13.14 |
| Pro | 1.28 | Pro | 10.51 |
| Ile | 1.28 | Thr | 3.69 |
| | | Gly | 0.50 |
| | | Cys | 0.19 |
| | | Ala | 0.13 |
| | | Asp | 0.13 |
| | | Ile | 0.13 |
| | | Val | 0.06 |
| | | Tyr | 0.06 |
| | | Glu | 0.06 |

Residue L 91 (Kabat)

BAT: Arg(R)  Germline: Tyr(Y)

| Mouse V$_x$VI | | All Mouse V$_x$ | |
|---|---|---|---|
| Residue | % Frequency | Residue | % Frequency |
| Trp | 80.63 | Trp | 20.41 |
| Arg | 8.75 | Gly | 19.33 |
| Gly | 6.25 | Ser | 18.76 |
| Phe | 1.88 | Tyr | 15.40 |
| Tyr | 1.25 | His | 8.49 |
| Asp | 0.62 | Asp | 4.37 |
| Ser | 0.62 | Phe | 3.36 |
| | | Arg | 2.47 |
| | | Asn | 1.90 |
| | | Leu | 1.52 |
| | | Thr | 0.82 |
| | | Val | 0.76 |
| | | Cys | 0.76 |
| | | Ala | 0.63 |
| | | Ile | 0.44 |
| | | Gln | 0.25 |
| | | Met | 0.19 |
| | | Other | 0.13 |

Fig. 4 cont. (5)

Residue L 92 (Kabat)

BAT: Ser(S)  Germline: His(H)

| Mouse V$_x$VI | | All Mouse V$_x$ | |
|---|---|---|---|
| Residue | % Frequency | Residue | % Frequency |
| Ser | 74.52 | Ser | 33.10 |
| Asn | 12.10 | Asn | 14.19 |
| Thr | 8.92 | Thr | 12.72 |
| Arg | 1.27 | Tyr | 12.46 |
| Tyr | 1.27 | His | 5.24 |
| Gly | 0.64 | Asp | 4.28 |
| His | 0.64 | Leu | 4.22 |
| Asp | 0.64 | Arg | 3.26 |
| | | Trp | 2.81 |
| | | Lys | 1.79 |
| | | Ala | 1.66 |
| | | Gly | 1.28 |
| | | Val | 1.09 |
| | | Gln | 0.83 |
| | | Ile | 0.58 |
| | | Cys | 0.26 |
| | | Phe | 0.19 |
| | | Met | 0.06 |

Residue L 94 (Kabat)

BAT: Phe(F)  Germline: Tyr(Y)

| Mouse V$_x$VI | | All Mouse V$_x$ | |
|---|---|---|---|
| Residue | % Frequency | Residue | % Frequency |
| Asn | 66.67 | Tyr | 19.54 |
| Tyr | 15.72 | Asn | 16.83 |
| Pro | 11.32 | Val | 14.89 |
| Ser | 3.77 | Leu | 13.35 |
| Ile | 0.63 | Ser | 6.90 |
| Leu | 0.63 | Phe | 6.45 |
| Lys | 0.63 | Thr | 6.25 |
| His | 0.63 | Asp | 4.96 |
| | | Ile | 4.00 |
| | | Trp | 2.39 |
| | | Ala | 0.97 |
| | | Pro | 0.84 |
| | | His | 0.58 |
| | | Gln | 0.52 |
| | | Met | 0.45 |
| | | Lys | 0.39 |
| | | Gly | 0.19 |
| | | Cys | 0.19 |
| | | Arg | 0.19 |
| | | Glu | 0.13 |

Fig 4 cont. (6)

Residue L 95F (Kabat)

BAT: Pro(P)  *Germline: Gap(-)*

| Mouse V$_x$VI | | All Mouse V$_x$ | |
|---|---|---|---|
| Residue | % Frequency | Residue | % Frequency |
| Arg | 100.00 | Thr | 98.30 |
|  |  | Pro | 0.35 |
|  |  | Ser | 0.28 |
|  |  | Met | 0.21 |
|  |  | Val | 0.21 |
|  |  | Phe | 0.21 |
|  |  | Leu | 0.14 |
|  |  | Ala | 0.07 |
|  |  | Arg | 0.07 |
|  |  | Lys | 0.07 |
|  |  | Other | 0.07 |

Residue L 96 (Kabat)

BAT: Leu(L)  *Germline: Phe(F)*

| Mouse V$_x$VI | | All Mouse V$_x$ | |
|---|---|---|---|
| Residue | % Frequency | Residue | % Frequency |
| Leu | 57.14 | Phe | 99.37 |
| Ile | 17.01 | Leu | 0.28 |
| Tyr | 7.48 | Gly | 0.21 |
| Trp | 6.80 | Arg | 0.07 |
| Phe | 5.44 | Val | 0.07 |
| Pro | 2.72 |  |  |
| Arg | 2.04 |  |  |
| His | 0.68 |  |  |
| Val | 0.68 |  |  |

Fig 5

```
AAGCTTGCCGCCACCATGGATTTACAGGTGCAGATTATCAGCTTCCTGCTAATCAGTGCC
TTCGAACGGCGGTGGTACCTAAATGTCCACGTCTAATAGTCGAAGGACGATTAGTCACGG
              M   D   L   Q   V   Q   I   I   S   F   L   L   I   S   A

TCAGTCATAATGTCCAGAGAGACAAATTGTTCTCACCCAGTCTCCAGCAATCATGTCTGCA
AGTCAGTATTACAGGTCTCTCTGTTTAACAAGAGTGGGTCAGAGGTCGTTAGTACAGACGT
  S   V   I   M   S   R   G   Q   I   V   L   T   Q   S   P   A   I   M   S   A

TCTCCAGGGGAGAAGGTCACCATAACCTGCAGTGCCAGTTCAAGTGTAAGTTACATGCAC
AGAGGTCCCCCTCTTCCAGTGGTATTGGACGTCACGGTCAAGTTCACATTCAATGTACGTG
  S   P   G   E   K   V   T   I   T   C   S   A   R   S   S   V   S   Y   M   H

TGGTTCCAGCAGAAGCCAGGCACTTCTCCCAAACTCTGGATTTATAGGACATCCAACCTG
ACCAAGGTCGTCTTCGGTCCGTGAAGAGGGTTTGAGACCTAAATATCCTGTAGGTTGGAC
  W   F   Q   Q   K   P   G   T   S   P   K   L   W   I   Y   R   T   S   N   L

GCTTCTGGAGTCCCTGCTCGCTTCAGTGGCAGTGGATCTGGGACCCTCTTACTGTCTCACA
CGAAGACCTCAGGGACGAGCGAAGTCACCGTCACCTAGACCCTGGAGAATGACAGAGTGT
  A   S   G   V   P   A   R   F   S   G   S   G   S   G   T   S   Y   C   L   T

ATCAGCCGAATGGAGGCTGAAGATGCTGCCACTTATTACTGCCAGCAAAGGAGTAGTTTC
TAGTCGGCTTACCTCCGACTTCTACGACGGTGAATAATGACGGTCGTTTCCTCATCAAAG
  I   S   R   M   E   A   E   D   A   A   T   Y   Y   C   Q   Q   R   S   S   F

CCACTCACGTTCGGCTCGGGGACAAAGTTGGAAATAAAACGTGAGTGGATCC
GGTGAGTGCAAGCCGAGCCCTGTTTCAACCTTTATTTTGCACTCACCTAGG
  P   L   T   F   G   S   G   T   K   L   E   I   K
```

Fig 6

```
AAGCTTGCCGCCACCATGGCTTGGGTGTGGACCTTGCTATTCCTGATGGCAGCTGCCCAA
TTCGAACGGCGGTGTACCGGAACCACACCTGGAACGATAAGGACTACCGTCGACGGGTT
            M  A  W  V  W  T  L  L  F  L  M  A  A  A  Q

AGTATCCAAGCACAGATCCAGTTGGTGCAGTCTGGACCTGAGTTGAAGAAGCCTGGAGAG
TCATAGGTTCGTGTCTAGGTCAACACGTCAGACCTGGACTCAACTTCTTCGGACCTCTC
 S  I  Q  A  Q  I  Q  L  V  Q  S  G  P  E  L  K  K  P  G  E

ACAGTCAAGATCTCCTGCAAGGCTTCTGGATATACTTTCACAAACTATGGAATGAACTGG
TGTCAGTTCTAGAGGACGTTCCGAAGACCTATATGAAAGTGTTTGATACCTTACTTGACC
 T  V  K  I  S  C  K  A  S  G  Y  T  F  T  N  Y  G  M  N  W

GTGAAGCAGGCTCCAGGAAAGGGTTTAAAGTGGATGGGCTGGATAAACACCGACAGTGGA
CACTTCGTCCGAGGTCCTTTCCCAAATTTCACCTACCCGACCTATTTGTGGCTGTCACCT
 V  K  Q  A  P  G  K  G  L  K  W  M  G  W  I  N  T  D  S  G

GAGTCAACATATGCTGAAGAGTTCAAGGGACGGTTTGCCTTCTCTTTGGAAACCTCTGCC
CTCAGTTGTATACGACTTCTCAAGTTCCCTGCCAAACGGAAGAGAAACCTTTGGAGACGG
 E  S  T  Y  A  E  E  F  K  G  R  F  A  F  S  L  E  T  S  A

AACACTGCCTATTTGCAGATCAACAACCTCAACAATGAGGACACGGCTACATATTTCTGT
TTGTGACGGATAAACGTCTAGTTGTTGGAGTTGTTACTCCTGTGCCGATGTATAAAGACA
 N  T  A  Y  L  Q  I  N  N  L  N  N  E  D  T  A  Y  F  C

GTGAGAGTCGGCTACGATGCTTTGGACTACTGGGGTCAAGGAACCTCAGTCACCGTCTCC
CACTCTCAGCCGATGCTACGAAACCTGATGACCCCAGTTCCTTGGAGTCAGTGGCAGAGG
 V  R  V  G  Y  D  A  L  D  Y  W  G  Q  G  T  S  V  T  V  S

TCAGGTGAGTGGATCC
AGTCCACTCACCTAGG
```

Peptide 1: TINEEEKC:

FIG.10

Peptide 1: NSGPSMRKKNVSIG

FIG.11

Peptide 1: IPDHQ

FIG.12

SEQUENCE LISTING

```
<160> NUMBER OF SEQ ID NOS: 37

<210> SEQ ID NO 1
<211> LENGTH: 408
<212> TYPE: DNA
<213> ORGANISM: Mus sp.

<400> SEQUENCE: 1
atggcttggg tgtggacctt gctattcctg atggcagctg cccaaagtat ccaagcacag      60
```

|  |  |  |  |  |
|---|---|---|---|---|
| atccagttgg | tgcagtctgg | acctgagttg | aagaagcctg | gagagacagt caagatctcc | 120 |
| tgcaaggctt | ctggatatac | tttcacaaac | tatggaatga | actgggtgaa gcaggctcca | 180 |
| ggaaagggtt | taaagtggat | gggctggata | acaccgaca | gtggagagtc aacatatgct | 240 |
| gaagagttca | agggacggtt | tgccttctct | ttggaaacct | ctgccaacac tgcctatttg | 300 |
| cagatcaaca | acctcaacaa | tgaggacacg | gctacatatt | tctgtgtgag agtcggctac | 360 |
| gatgctttgg | actactgggg | tcaaggaacc | tcagtcaccg | tctcctca | 408 |

<210> SEQ ID NO 2
<211> LENGTH: 136
<212> TYPE: PRT
<213> ORGANISM: Mus sp.

<400> SEQUENCE: 2

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asp Ser Gly Glu Ser Thr Tyr Ala
65                  70                  75                  80

Glu Glu Phe Lys Gly Arg Phe Ala Phe Ser Leu Glu Thr Ser Ala Asn
                85                  90                  95

Thr Ala Tyr Leu Gln Ile Asn Asn Leu Asn Asn Glu Asp Thr Ala Thr
            100                 105                 110

Tyr Phe Cys Val Arg Val Gly Tyr Asp Ala Leu Asp Tyr Trp Gly Gln
        115                 120                 125

Gly Thr Ser Val Thr Val Ser Ser
    130                 135

<210> SEQ ID NO 3
<211> LENGTH: 384
<212> TYPE: DNA
<213> ORGANISM: Mus sp.

<400> SEQUENCE: 3

|  |  |  |  |  |
|---|---|---|---|---|
| atggatttac | aggtgcagat | tatcagcttc | ctgctaatca | gtgcctcagt cataatgtcc | 60 |
| agaggacaaa | ttgttctcac | ccagtctcca | gcaatcatgt | ctgcatctcc aggggagaag | 120 |
| gtcaccataa | cctgcagtgc | caggtcaagt | gtaagttaca | tgcactggtt ccagcagaag | 180 |
| ccaggcactt | ctcccaaact | ctggatttat | aggacatcca | acctggcttc tggagtccct | 240 |
| gctcgcttca | gtggcagtgg | atctgggacc | tcttactgtc | tcacaatcag ccgaatggag | 300 |
| gctgaagatg | ctgccactta | ttactgccag | caaaggagta | gtttcccact cacgttcggc | 360 |
| tcggggacaa | agttggaaat | aaaa | | | 384 |

<210> SEQ ID NO 4
<211> LENGTH: 128
<212> TYPE: PRT
<213> ORGANISM: Mus sp.

<400> SEQUENCE: 4

Met Asp Leu Gln Val Gln Ile Ile Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Arg
        35                  40                  45

Ser Ser Val Ser Tyr Met His Trp Phe Gln Gln Lys Pro Gly Thr Ser
    50                  55                  60

Pro Lys Leu Trp Ile Tyr Arg Thr Ser Asn Leu Ala Ser Gly Val Pro
65                  70                  75                  80

Ala Arg Phe Ser Gly Ser Gly Ser Gly Thr Ser Tyr Cys Leu Thr Ile
                85                  90                  95

Ser Arg Met Glu Ala Glu Asp Ala Ala Thr Tyr Tyr Cys Gln Gln Arg
            100                 105                 110

Ser Ser Phe Pro Leu Thr Phe Gly Ser Gly Thr Lys Leu Glu Ile Lys
        115                 120                 125

<210> SEQ ID NO 5
<211> LENGTH: 384
<212> TYPE: DNA
<213> ORGANISM: Mus sp.

<400> SEQUENCE: 5 atggattac aggtgcagat tatcagcttc ctgctaatca gtgcctcagt cataatgtcc      60
agaggacaaa ttgttctcac ccagtctcca gcaatcatgt ctgcatctcc aggggagaag    120
gtcaccataa cctgcagtgc caggtcaagt gtaagttaca tgcactggtt ccagcagaag    180
ccaggcactt ctcccaaact ctggatttat aggacatcca acctggcttc tggagtccct    240
gctcgcttca gtggcagtgg atctgggacc tcttactgtc tcacaatcag ccgaatggag    300
gctgaagatg ctgccactta ttactgccag caaaggagta gtttcccact cacgttcggc    360
tcggggacaa agttggaaat aaaa                                            384

<210> SEQ ID NO 6
<211> LENGTH: 128
<212> TYPE: PRT
<213> ORGANISM: Mus sp.

<400> SEQUENCE: 6

Met Asp Leu Gln Val Gln Ile Ile Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Arg
        35                  40                  45

Ser Ser Val Ser Tyr Met His Trp Phe Gln Gln Lys Pro Gly Thr Ser
    50                  55                  60

Pro Lys Leu Trp Ile Tyr Arg Thr Ser Asn Leu Ala Ser Gly Val Pro
65                  70                  75                  80

Ala Arg Phe Ser Gly Ser Gly Ser Gly Thr Ser Tyr Cys Leu Thr Ile
                85                  90                  95

Ser Arg Met Glu Ala Glu Asp Ala Ala Thr Tyr Tyr Cys Gln Gln Arg
            100                 105                 110

Ser Ser Phe Pro Leu Thr Phe Gly Ser Gly Thr Lys Leu Glu Ile Lys
        115                 120                 125

<210> SEQ ID NO 7
<211> LENGTH: 408

```
<212> TYPE: DNA
<213> ORGANISM: Mus sp.

<400> SEQUENCE: 7
atggcttggg tgtggacctt gctattcctg atggcagctg cccaaagtat ccaagcacag    60
atccagttgg tgcagtctgg acctgagttg aagaagcctg agagacagt caagatctcc   120 tgcaaggctt ctggatatac tttcacaaac tatggaatga actgggtgaa gcaggctcca   180
ggaaagggtt taaagtggat gggctggata acaccgaca gtggagagtc aacatatgct    240
gaagagttca aggacggtt tgccttctct ttggaaacct ctgccaacac tgcctatttg     300
cagatcaaca acctcaacaa tgaggacacg gctacatatt tctgtgtgag agtcggctac   360
gatgctttgg actactgggg tcaaggaacc tcagtcaccg tctcctca                408

<210> SEQ ID NO 8
<211> LENGTH: 136
<212> TYPE: PRT
<213> ORGANISM: Mus sp.

<400> SEQUENCE: 8

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asp Ser Gly Glu Ser Thr Tyr Ala
65                  70                  75                  80

Glu Glu Phe Lys Gly Arg Phe Ala Phe Ser Leu Glu Thr Ser Ala Asn
                85                  90                  95

Thr Ala Tyr Leu Gln Ile Asn Asn Leu Asn Asn Glu Asp Thr Ala Thr
            100                 105                 110

Tyr Phe Cys Val Arg Val Gly Tyr Asp Ala Leu Asp Tyr Trp Gly Gln
        115                 120                 125

Gly Thr Ser Val Thr Val Ser Ser
    130                 135

<210> SEQ ID NO 9
<211> LENGTH: 8
<212> TYPE: PRT
<213> ORGANISM: homo sapiens

<400> SEQUENCE: 9

Thr Ile Asn Glu Glu Glu Lys Cys
1               5

<210> SEQ ID NO 10
<211> LENGTH: 14
<212> TYPE: PRT
<213> ORGANISM: homo sapiens

<400> SEQUENCE: 10

Asn Ser Gly Pro Ser Met Arg Lys Lys Asn Val Ser Ile Gly
1               5                   10

<210> SEQ ID NO 11
<211> LENGTH: 5
```

```
<212> TYPE: PRT
<213> ORGANISM: homo sapiens

<400> SEQUENCE: 11

Ile Pro Asp His Gln
1               5

<210> SEQ ID NO 12
<211> LENGTH: 30
<212> TYPE: DNA
<213> ORGANISM: Mus sp.

<400> SEQUENCE: 12
atggactcca ggctcaattt agttttcctt                                    30

<210> SEQ ID NO 13
<211> LENGTH: 30
<212> TYPE: DNA
<213> ORGANISM: Mus sp.

<400> SEQUENCE: 13
atggmttggg tgtggamctt gctattcctg                                    30

<210> SEQ ID NO 14
<211> LENGTH: 21
<212> TYPE: DNA
<213> ORGANISM: Mus sp.

<400> SEQUENCE: 14
caagggatag acagatgggg c                                             21

<210> SEQ ID NO 15
<211> LENGTH: 30
<212> TYPE: DNA
<213> ORGANISM: Mus sp.

<400> SEQUENCE: 15
atggagwcag acacactcct gytatgggtg                                    30

<210> SEQ ID NO 16
<211> LENGTH: 30
<212> TYPE: DNA
<213> ORGANISM: Mus sp.

<400> SEQUENCE: 16
atggatttwc aggtgcagat twtcagcttc                                    30

<210> SEQ ID NO 17
<211> LENGTH: 27
<212> TYPE: DNA
<213> ORGANISM: Mus sp.

<400> SEQUENCE: 17
atgaggtkcy ytgytsagyt yctgrgg                                       27

<210> SEQ ID NO 18
<211> LENGTH: 28
<212> TYPE: DNA
<213> ORGANISM: Mus sp.

<400> SEQUENCE: 18
atggaagccc cagctcagct tctcttcc                                      28
```

<210> SEQ ID NO 19
<211> LENGTH: 20
<212> TYPE: DNA
<213> ORGANISM: Mus sp.

<400> SEQUENCE: 19
actggatggt gggaagatgg                                               20

<210> SEQ ID NO 20
<211> LENGTH: 18
<212> TYPE: DNA
<213> ORGANISM: Artificial Sequence
<220> FEATURE:
<223> OTHER INFORMATION: PCR forward primer (Table 3)

<400> SEQUENCE: 20
ctagatgcat gctcgagc                                                 18

<210> SEQ ID NO 21
<211> LENGTH: 21
<212> TYPE: DNA
<213> ORGANISM: Artificial Sequence
<220> FEATURE:
<223> OTHER INFORMATION: PCR reverse primer (Table 3)

<400> SEQUENCE: 21
taccgagctc ggatccacta g                                             21

<210> SEQ ID NO 22
<211> LENGTH: 42
<212> TYPE: DNA
<213> ORGANISM: Mus sp.

<400> SEQUENCE: 22
cccaagcttg ccgccaccat ggattttcag gtgcagatta tc                      42

<210> SEQ ID NO 23
<211> LENGTH: 39
<212> TYPE: DNA
<213> ORGANISM: Mus sp.

<400> SEQUENCE: 23
cgcggatcca ctcacgtttt atttccaact ttgtccccg                          39

<210> SEQ ID NO 24
<211> LENGTH: 40
<212> TYPE: DNA
<213> ORGANISM: Mus sp.

<400> SEQUENCE: 24
ggatccactc acctgaggag acggtgactg aggttccttg                         40

<210> SEQ ID NO 25
<211> LENGTH: 42
<212> TYPE: DNA
<213> ORGANISM: Mus sp.

<400> SEQUENCE: 25
aagcttgccg ccaccatggc ttgggtgtgg accttgctat tc                      42

<210> SEQ ID NO 26
<211> LENGTH: 17
<212> TYPE: DNA
<213> ORGANISM: Artificial Sequence
<220> FEATURE:

-continued

<223> OTHER INFORMATION: Hu-gamma1 primer (Table 5)

<400> SEQUENCE: 26
ttggaggagg gtgccag                                                17

<210> SEQ ID NO 27
<211> LENGTH: 28
<212> TYPE: DNA
<213> ORGANISM: Artificial Sequence
<220> FEATURE:
<223> OTHER INFORMATION: HCMVi3s primer (Table 5)

<400> SEQUENCE: 27
gtcaccgtcc ttgacacgcg tctcggga                                    28

<210> SEQ ID NO 28
<211> LENGTH: 18
<212> TYPE: DNA
<213> ORGANISM: Artificial Sequence
<220> FEATURE:
<223> OTHER INFORMATION: forward primer (Table 5)

<400> SEQUENCE: 28
tgtaaaacga cggccagt                                               18

<210> SEQ ID NO 29
<211> LENGTH: 18
<212> TYPE: DNA
<213> ORGANISM: Artificial Sequence
<220> FEATURE:
<223> OTHER INFORMATION: reverse primer (Table 5)

<400> SEQUENCE: 29
gaaacagcta tgaccatg                                               18

<210> SEQ ID NO 30
<211> LENGTH: 27
<212> TYPE: DNA
<213> ORGANISM: Mus sp.

<400> SEQUENCE: 30
cagcatatgt tgactctcca ctgtcgg                                     27

<210> SEQ ID NO 31
<211> LENGTH: 27
<212> TYPE: DNA
<213> ORGANISM: Mus sp.

<400> SEQUENCE: 31
gtcaacatat gctgaagagt tcaaggg                                     27

<210> SEQ ID NO 32
<211> LENGTH: 18
<212> TYPE: DNA
<213> ORGANISM: Mus sp.

<400> SEQUENCE: 32
tgccaggtca agtgtaag                                               18

<210> SEQ ID NO 33
<211> LENGTH: 18
<212> TYPE: DNA
<213> ORGANISM: Mus sp.

<400> SEQUENCE: 33

```
aagccaggtt ggatgtcc                                                       18
```

<210> SEQ ID NO 34
<211> LENGTH: 130
<212> TYPE: PRT
<213> ORGANISM: Mus sp.
<220> FEATURE:
<221> NAME/KEY: MISC_FEATURE
<222> LOCATION: (36)..(36)
<223> OTHER INFORMATION: Xaa can be any naturally occurring amino acid
<220> FEATURE:
<221> NAME/KEY: MISC_FEATURE
<222> LOCATION: (55)..(55)
<223> OTHER INFORMATION: Xaa can be any naturally occurring amino acid
<220> FEATURE:
<221> NAME/KEY: MISC_FEATURE
<222> LOCATION: (106)..(116)
<223> OTHER INFORMATION: Xaa can be any naturally occurring amino acid

<400> SEQUENCE: 34

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
             20                  25                  30

Gly Met Asn Xaa Trp Val Lys Gln Ala Pro Gly Lys Gly Leu Lys Trp
         35                  40                  45

Met Gly Trp Ile Asn Thr Xaa Asp Ser Gly Glu Ser Thr Tyr Ala Glu
     50                  55                  60

Glu Phe Lys Gly Arg Phe Ala Phe Ser Leu Glu Thr Ser Ala Asn Thr
 65                  70                  75                  80

Ala Tyr Leu Gln Ile Asn Asn Leu Asn Asn Glu Asp Thr Ala Thr Tyr
                 85                  90                  95

Phe Cys Val Arg Val Gly Tyr Asp Ala Xaa Xaa Xaa Xaa Xaa Xaa Xaa
            100                 105                 110

Xaa Xaa Xaa Xaa Leu Asp Tyr Trp Gly Gln Gly Thr Ser Val Thr Val
        115                 120                 125

Ser Ser
    130
```

<210> SEQ ID NO 35
<211> LENGTH: 130
<212> TYPE: PRT
<213> ORGANISM: Mus sp.
<220> FEATURE:
<221> NAME/KEY: MISC_FEATURE
<222> LOCATION: (36)..(36)
<223> OTHER INFORMATION: Xaa can be any naturally occurring amino acid
<220> FEATURE:
<221> NAME/KEY: MISC_FEATURE
<222> LOCATION: (55)..(55)
<223> OTHER INFORMATION: Xaa can be any naturally occurring amino acid
<220> FEATURE:
<221> NAME/KEY: MISC_FEATURE
<222> LOCATION: (109)..(113)
<223> OTHER INFORMATION: Xaa can be any naturally occurring amino acid

<400> SEQUENCE: 35

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
             20                  25                  30

Gly Met Asn Xaa Trp Val Lys Gln Ala Pro Gly Lys Gly Leu Lys Trp
         35                  40                  45
```

```
Met Gly Trp Ile Asn Thr Xaa Asn Thr Gly Glu Pro Thr Tyr Ala Glu
 50                  55                  60

Glu Phe Lys Gly Arg Phe Ala Phe Ser Leu Glu Thr Ser Ala Ser Thr
 65                  70                  75                  80

Ala Tyr Leu Gln Ile Asn Asn Leu Lys Asn Glu Asp Thr Ala Thr Tyr
                 85                  90                  95

Phe Cys Ala Arg Arg Gly Tyr Tyr Tyr Gly Ser Arg Xaa Xaa Xaa Xaa
                100                 105                 110

Xaa Tyr Gly Ala Met Asp Tyr Trp Gly Gln Gly Thr Ser Val Thr Val
            115                 120                 125

Ser Ser
    130

<210> SEQ ID NO 36
<211> LENGTH: 120
<212> TYPE: PRT
<213> ORGANISM: Mus sp.
<220> FEATURE:
<221> NAME/KEY: MISC_FEATURE
<222> LOCATION: (28)..(34)
<223> OTHER INFORMATION: Xaa can be any naturally occurring amino acid
<220> FEATURE:
<221> NAME/KEY: MISC_FEATURE
<222> LOCATION: (102)..(106)
<223> OTHER INFORMATION: Xaa can be any naturally occurring amino acid
<220> FEATURE:
<221> NAME/KEY: MISC_FEATURE
<222> LOCATION: (119)..(119)
<223> OTHER INFORMATION: Xaa can be any naturally occurring amino acid

<400> SEQUENCE: 36

Gln Ile Val Leu Thr Gln Ser Pro Ala Ile Met Ser Ala Ser Pro Gly
 1               5                  10                  15

Glu Lys Val Thr Ile Thr Cys Ser Ala Arg Ser Xaa Xaa Xaa Xaa Xaa
                 20                  25                  30

Xaa Xaa Ser Val Ser Tyr Met His Trp Phe Gln Lys Pro Gly Thr
             35                  40                  45

Ser Pro Lys Leu Trp Ile Tyr Arg Thr Ser Asn Leu Ala Ser Gly Val
 50                  55                  60

Pro Ala Arg Phe Ser Gly Ser Gly Ser Gly Thr Ser Tyr Cys Leu Thr
 65                  70                  75                  80

Ile Ser Arg Met Glu Ala Glu Asp Ala Ala Thr Tyr Tyr Cys Gln Gln
                 85                  90                  95

Arg Ser Ser Phe Pro Xaa Xaa Xaa Xaa Xaa Pro Leu Thr Phe Gly Ser
                100                 105                 110

Gly Thr Lys Leu Glu Ile Xaa Lys
            115                 120

<210> SEQ ID NO 37
<211> LENGTH: 120
<212> TYPE: PRT
<213> ORGANISM: Mus sp.
<220> FEATURE:
<221> NAME/KEY: MISC_FEATURE
<222> LOCATION: (28)..(34)
<223> OTHER INFORMATION: Xaa can be any naturally occurring amino acid
<220> FEATURE:
<221> NAME/KEY: MISC_FEATURE
<222> LOCATION: (102)..(106)
<223> OTHER INFORMATION: Xaa can be any naturally occurring amino acid
<220> FEATURE:
<221> NAME/KEY: MISC_FEATURE
<222> LOCATION: (119)..(119)
<223> OTHER INFORMATION: Xaa can be any naturally occurring amino acid
```

```
<400> SEQUENCE: 37

Gln Ile Val Leu Thr Gln Ser Pro Ala Ile Met Ser Ala Ser Pro Gly
1               5                   10                  15

Glu Lys Val Thr Ile Ser Cys Ser Ala Ser Xaa Xaa Xaa Xaa Xaa
            20                  25                  30

Xaa Xaa Ser Val Ser Tyr Met Tyr Trp Tyr Gln Gln Lys Pro Gly Ser
        35                  40                  45

Ser Pro Lys Pro Trp Ile Tyr Arg Thr Ser Asn Leu Ala Ser Gly Val
    50                  55                  60

Pro Ala Arg Phe Ser Gly Ser Gly Ser Gly Thr Ser Tyr Ser Leu Thr
65                  70                  75                  80

Ile Ser Ser Met Glu Ala Glu Asp Ala Ala Thr Tyr Tyr Cys Gln Gln
                85                  90                  95

Tyr His Ser Tyr Pro Xaa Xaa Xaa Xaa Xaa Pro Phe Thr Phe Gly Ser
            100                 105                 110

Gly Thr Lys Leu Glu Ile Xaa Lys
            115                 120
```

MONOCLONAL ANTIBODIES, ANTIGENS AND DIAGNOSIS AND THERAPY OF MALIGNANT DISEASES

CROSS-REFERENCE TO RELATED APPLICATION

This application is a divisional of application Ser. No. 09/967,719, filed Sep. 28, 2001, now abandoned, which is a continuation of the U.S. National Stage designation of International Application PCT/IL99/00518 filed Sep. 30, 1999, designating the U.S., the content of which is expressly incorporated herein by reference hereto.

FIELD OF THE INVENTION

The present invention concerns novel sequences of monoclonal antibodies, peptidic sequences of antigens to which the monoclonal antibodies bind, as well as diagnostic and therapeutic assays using the monoclonal antibody and peptides.

BACKGROUND OF THE INVENTION

Co-owned PCT Application, Publication No. WO 95/20605, discloses immuno-stimulatory monoclonal antibodies. The antibodies subject of this PCT application were raised against B lymphoblastoid cells and were shown to have an immuno-stimulatory effect. When injected into tumor-bearing animals, these antibodies were also found to elicit an anti-tumor effect.

Cancer diagnosis, under current medical procedures, is typically a multi-step process involving physical examination, use of a variety of imaging techniques, employment of a variety of cancer markers, etc. There is a longfelt need in the art for cancer diagnostic techniques which allow detection of cancer and also determination of the type of cancer which the tested individual is suffering from.

GENERAL DESCRIPTION OF THE INVENTION

The present invention is based on the finding of sequences of monoclonal antibodies against lymphoblastoid cells. The present invention is further based on the finding that the level of binding of these antibodies to T-cells of patients having cancer is different (higher or lower) than the level of binding of these antibodies to T-cells of healthy individuals.

In accordance with one aspect of the invention there is provided a monoclonal antibody having a variable region selected from the group consisting of:

(a) a monoclonal antibody having a heavy chain variable region comprising the amino acid sequence of FIG. 1 (SEQ ID NO:2);

(b) a monoclonal antibody having a Kappa light chain variable region comprising the amino acid sequence of FIG. 2 (SEQ ID NO:4);

(c) a monoclonal antibody having a heavy chain variable region comprising the amino acid sequence of FIG. 1 (SEQ ID NO:2) and the Kappa light chain variable region comprising the amino acid sequence of FIG. 2 (SEQ ID NO:4);

(d) a monoclonal antibody having a heavy chain variable region having at least 70% identity to the amino acid sequence of FIG. 1;

(e) a monoclonal antibody having a light chain variable region having at least 70% identity to the sequence of FIG. 2.

In accordance with the invention, the term "antibody" refers to monoclonal antibodies of any of the classes IgG, IgM, IgD, IgA and IgE. The term refers to whole antibodies or fragments of the antibodies comprising the antigen-binding domain of the antibodies, e.g. antibodies lacking the Fc portion, single chain antibodies, fragments of articles consisting essentially of only the variable antigen-binding domain of the antibody, etc.

In addition the invention also concerns antibodies which bind to an antigen to which any one of the above mAbs specifically binds to i.e. antibodies which have cross reactivity with the above antibodies.

In accordance with one embodiment of the invention, the monoclonal antibody is a chimeric human-mouse antibody, namely a mAb with a constant region derived from a human origin and a variable region derived from mouse. For this purpose, the Kappa light and heavy chain variable regions of the mAb of the invention were PCR cloned and their DNA sequenced. In accordance with yet another embodiment of the invention the antibody is a fully humanized antibody, i.e. both its variable and constant region are derived from a human source.

The term "having at least X percent identity" refers to the percent of amino acid residues that are identical in the two compared sequences when the sequences are optimally aligned. Thus, 70% amino acid sequence identity means that 70% of the amino acids in two or more optimally aligned polypeptide sequences are identical. Preferably, the identity is at least 80%, most preferably at least 90%.

In accordance with an additional aspect of the invention, there are provided mouse hybridoma cell lines which produce any of the mAbs of the invention. The hybridomas may be prepared by any of the methods known in the art (for example, Kohler, G. and Milstein, C., *Nature*, 256:495-497, (1975)). The supernatant of the hybridoma cell lines are typically screened for antibody binding activity by any one of the methods known in the art such as by enzyme linked immuno sorbent assay (ELISA) or radio immuno assay (RIA). The supernatants are screened for production of mAbs which bind to any of the peptides of the invention (as explained below) or which bind to cells to which they bind, e.g. Daudi cells or T lymphocytes.

DNA sequences which encode any of the amino acid sequences of the heavy chain or light chain of the above mAbs are also encompassed within the scope of the invention. As will no doubt be clear to any man versed in the art, due to the degenerative nature of the genetic code a plurality of nucleic acid sequences may code for the mAb of the invention beyond those shown in FIG. 1 or 2.

The invention also provides expression vectors such as plasmids having said DNA sequences as well as host cells containing one or more of these expression vectors.

In accordance with another aspect of the invention, there are provided peptidic sequences of a B-cell antigens to which the mAbs of the invention can bind. Searches performed against the non-redundant gene bank database and the EST division determined that these peptidic sequences are novel.

In accordance with this additional aspect of the invention there is provided a peptide selected from the group consisting of:

(a) a peptide having an amino acid sequence as depicted in FIG. 10 (SEQ ID NO:9);

(b) a peptide having an amino acid sequence as depicted in FIG. 11 (SEQ ID NO:10);

(c) a peptide having an amino acid sequence as depicted in FIG. 12 (SEQ ID NO:11);

(d) a peptide having at least 85% identity to any one of the amino acid sequences of the peptides of (a), (b) and (c) above; and (e) a protein or a peptide comprising one or more of the peptides of (a)-(d) above.

The peptides of the invention may be used for a variety of diagnostic assays, such as, for example, competitive immuno-assays wherein the level of binding of the mAb of the invention to its native antigen, which exists on T-cells is determined. In addition, the peptides may be used for the production of antibodies in immunized animals which antibodies may then be used for any one of the utilities described above and below.

Analogs of all the above peptides also form an additional aspect of the present invention. As will be appreciated by an person versed in the art, the amino acid sequence of the peptides of the invention may be altered, for example, by addition, deletion or conservative or non-conservative substitution of one or more amino acids without substantially altering the antibody binding properties of the peptide The term "conservative substitution" refers to the substitution of an amino acid in one class by an amino acid of the same class, where a class if defined by common physiochemical amino acid side chain properties and high substitution frequencies in homologous proteins found in nature, as determined, for example, by a standard Dayhoff frequency exchange matrix or BLOSUM matrix. [Six general classes of amino acid side chains have been characterized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another Class III residue such as Asn, Gln, or Glu, is a conservative substitution. The term "non-conservative substitution" refers to the substitution of an amino acid in one class with an amino acid from another class; for example, substitution of an Ala, a Class II residue, with a Class III residue such as Asp, Asn, Glu, or Gln.

The letters used above (and hereinafter) to denote specific amino acids (aa) are in accordance with the 1-letter amino acid symbols recommend by the IUPAC-IUB Biochemical Nomenclature Commission.

Analogs of the above peptides which fall under the scope of the present invention are such which have substantially the same level of binding to the mAbs of the invention as the peptides depicted in FIGS. 10-12 (SEQ ID NOS:9-11). The level of binding can be determined by any manner known in the art.

The peptides and analogs of the invention may also be chemically modified and such chemically modified peptides and analogues also form a part of the invention. The term "chemically modified" refers to a protein where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a liquid or lipid derivative, methylation, myristylation, pegylation, prenylation, phosphorylation, ubiqutination, or any similar process.

The second finding on which the invention is based is that the mAbs of the invention can bind to a different extent to T-cells obtained from individuals having a malignant disease as compared to the extent of binding of the same mAbs to T-cells of a healthy individual.

Thus, by a further aspect of the present invention an assay is provided for identifying a tested individual with a high probability of having a malignant disease comprising:

(a) obtaining a body fluid sample from said individual;
(b) contacting said sample with at least one mAb of the invention;
(c) determining the extent of binding of said mAbs to T-cells within said sample; and
(d) comparing the extent of (c) to the extent of binding of the mAbs of the invention to T-cells in a sample obtained from a healthy individual; a significant difference between the above two extents of binding indicating that said tested individual has a high probability of having a malignant disease.

In accordance with the invention, the sample obtained from the individual to be tested may be any body fluid which contains a detectable amount of T-cells. Typically, the body fluid sample is a blood or lymph fluid sample. Preferably, before contacting the mAbs of the invention with the obtained sample, the peripheral blood monoclear cells (PBMC) in the sample are separated by any one of the methods known in the art such as by Ficoll Hypaque density centrifugation and the separated cells are then contacted with the tested antibodies.

The term "malignant disease" in accordance with the invention is to be understood as any kind of malignant disease known in the art at any of its stages.

This term also encompasses malignant diseases which are at their early stages and have not yet elicited clinical symptoms. Preferably this term refers to solid tumors.

The term "healthy individual" relates to an individual who does not have a malignant disease, and may also refer to an average level of several individuals or to a level obtained by pooling together body fluids from several individuals. It should be noted that once a standard extent of binding of healthy individuals is established, there is no need to reestablish this standard for every test and the figure established may be used continuously. In accordance with the invention it has been found that in healthy individuals about 25% of $CD3^+$ T-cells bind to antibodies of the invention.

The term "high probability" means that the assay of the invention is an initial screening assay capable of identifying individuals suspected of having a malignant disease. The fact that the individual detected by the method of the invention has indeed a malignant disease will have to be verified later by utilizing additional techniques known in the art.

The term "extent of binding" relates to the level of binding of the antibody to an antigen present on the T-cell of the tested individual which extent can be determined by any of the methods known in the art for determining binding levels of antibodies such as ELISA or Western Blotting. The extent of binding may be determined using any detection system such as anti-mouse immunoglobulin or fragments thereof linked to a detectable marker. Examples of such detectable markers are a radioactive group, a fluorescent group, an enzyme capable of catalyzing a reaction yielding a detectable product (such as a color reaction), a biotin group capable of being detected by avidin, etc. By a preferred embodiment, the extent of binding of the mAbs of the invention to the T-cells is carried out by double labeling in which the anti T-cell antibody (e.g. anti-$CD3^+$ antibody) is attached to one kind of fluorescent marker and the mAb of the invention is attached to a second type of fluorescent marker. The extent of binding is then determined using fluorecein activated cell sorter (FACS). The quantitation of the extent of binding is achieved by determining the percent of $CD3^+$ T-cells (determined by their binding of anti-$CD3^+$ antibodies) which also bind the mAb of the invention.

In accordance with the invention, it was found that the total number of $CD3^+$ cells in blood samples of individuals having a malignant disease is similar to the number of $CD3^+$ cells in blood samples obtained from healthy individuals so that the normalization of the extent of binding of both mAb and $CD3^+$ T-cells by using total CD3+ binding T-cells both in malignant patients and healthy individuals is valid. However, the percent of the CD3+ binding T-cells which also bind the mAb of the invention (hereinafter: "CD3+ mAb cells") in individuals having a malignant disease differs significantly from the percent of CD3+ mAb+ cells in blood of healthy individuals. The percent of the CD3+ mAb+ cells in an individual having a malignant disease may either be significantly higher or significantly lower than the percent of CD3+ mAb+ cells in healthy individuals, depending on the type of the malignant disease.

The extent of binding of a mAb of the invention to a T-cell obtained from a tested individual will be considered to be "significantly different" than the extent of binding to T-cells obtained from a healthy individual when the difference in binding of the mAb is statistically different in a significant degree as determined by any of the statistical methods known in the art (e.g. Students t-Test) which are used in connection with results obtained by the experimental methods mentioned herewith.

The invention not only enables to identify individuals having a high probability of having any type of malignant diseases (where the diseased individual has a different extent of binding of T-cells to mAbs of the invention as compared to a healthy individual) but can also help identify individuals having specific types of cancer by determining whether said extent is higher or lower than the corresponding extent in the healthy individual.

Typically, the percent of binding of the mAbs of the invention to T-cells obtained from healthy individuals is in the range of about 25%, i.e. 25% of the cells expressing the CD3+ T-cell marker (determined by binding of anti-CD3+ antibody to the cells) also bind the mAbs of the invention.

In accordance with the invention, it has been shown that in samples obtained from prostate cancer patients, the percent of CD3+ T-cells to which the mAbs of the invention bind are in the range of about 50%.

It was further shown that where the CD3+ T-cells originate from samples obtained from colon or breast carcinoma patients, the percent of the cells which also bind to the mAbs of the invention is about 7% and 10%, respectively.

Thus, in accordance with the present invention it has become possible to determine that there is a high probability that there exists a specific type of cancer in a body fluid sample taken from a tested individual using a simple and single assay based on the extent of binding of the mAbs of the invention to CD3+ cells present in the body fluid sample. The simplicity of the diagnostic assay of the invention which necessitates use of only one kind of mAb to identify an individual having a certain type of cancer is very useful for wide screening of a population.

Thus, the present invention by another of its aspects provides an assay for identifying a tested individual with a high probability of having a specific malignant disease comprising:

(a) obtaining a body fluid sample from said individual;

(b) contacting said sample with the mAbs of the invention;

(c) determining the extent of binding of said mAbs to T-cells in said sample; and (d) comparing the extent of binding (c) cells obtained to the extent of binding of the mAbs to T-cells obtained from a healthy individual, the existence of a significant difference in the extents of binding indicating with a high probability that the tested individual has a malignant disease wherein whether the extent of binding to the T-cells from said individual is above or below the extent of the binding of the mAbs in T-cells of healthy individuals, indicates a specific type of malignant disease which the tested individual has with high probability.

In particular, where the extent of binding to the mAb of the invention is significantly higher than in healthy individuals the tested individual has a high probability of having prostate cancer.

Where the extent of binding is significantly lower than the healthy individual, the tested individual has a high probability of having colon or breast cancer.

In accordance with the diagnostic aspect of the invention, compositions comprising the mAbs of the invention may be used for diagnosis to identify individuals with the high probability of having a malignant disease (in general) or for identifying a specific malignant disease the individual is likely to have. The invention therefore provides by another of its aspects, a diagnostic composition comprising mAbs belonging to at least one of the abovementioned antibodies together with a suitable carrier. The carrier may either be a soluble carrier such as any one of the physiological acceptable buffers known in the art (e.g. PBS) or a solid state carrier such as, for example, latex beads.

The present invention also provides kits, e.g. diagnostic assay kits, for utilizing the mAbs of the invention and carrying out the diagnostic assays disclosed above. In one embodiment, the diagnostic kit would conventionally include at least one of the above mAbs in one or more containers, a conjugate of a specific binding partner for the mAb (for example the antigen or analog of the invention), a label capable of producing a detectable signal and directions for its use. The label may be, a priori, bound to the monoclonal antibody or, alternatively, the label may be bound to a carrier molecule which then specifically binds to the mAb. The incubation of the tested sample with the diagnostic reagent composition is for a time sufficient to allow binding of the monoclonal antibodies to the cells.

By a further aspect of the invention, there are provided pharmaceutical compositions comprising, as an active ingredient, one or more of the mAbs of the invention together. Use of said mAbs for the preparation of pharmaceutical preparations for the treatment of various malignant diseases in an individual is also within the scope of the invention.

By yet another aspect the present invention concerns a method of treatment of malignant diseases by administering to an individual in need a therapeutically effective amount of said mAbs. A therapeutically effective amount being an amount capable of alleviating the symptoms of the malignant disease, reducing the symptoms or completely eliminating them.

Pharmaceutical compositions comprising the peptides of the invention also constitute an aspect of the invention. Such compositions may be used, for example, for active immunization of an individual to obtain antibodies which may then bind to the T-cells of the individual and elicit an immune response in the individual.

DETAILED DESCRIPTION OF THE ASPECTS OF THE INVENTION

The main aspects of the invention will now be described with occasional reference to the attached figures. In the following description and figures, the term "BAT antibody" will be used interchangeably with the term "mAbs of the invention".

BRIEF DESCRIPTION OF THE FIGURES

FIG. 1 shows the DNA (SEQ ID NO:1) and peptide (SEQ ID NO:2) sequences of the heavy chain variable region of the mAb of the invention.

FIG. 2 shows DNA (SEQ ID NO:3) and peptide (SEQ ID NO:4) sequences of the Kappa light chain variable region of the mAb of the invention.

FIG. 3 shows an analysis of the amino acid sequence of the heavy chain variable region of the antibody of the invention (designated "BAT "BAT" defines the amino acid sequence of the BAT antibody $V_H$ region (SEQ ID NO:34), while "VMS2" defines the amino acid sequence of the germline VMS2/VGK4 germline gene (SEQ ID NO:35). Where the BAT sequence and the germline sequence are identical the germline sequence is represented by a dot (.); where mismatches occur the different germline residue is shown. The tables below, the sequence on the following pages describe the frequency with which certain amino acids have been seen at a particular residue position both within the Kabat et al., *Sequences of proteins of immunological interest*, (1991) mouse heavy chain subgroup miscellaneous (Mouse $V_H$ Misc.) and across a larger database of all known mouse $V_H$ sequences (All Mouse $V_H$).

FIG. 4 shows an analysis of the amino acid sequence of the kappa light chain variable region of the antibody of the invention (designated in the Fig. As "BAT") (SEQ ID NO:36). "Mouse" defines the amino acid sequence of the BAT antibody $K_K$ region, while "Germ" defines the amino acid sequence of the germline H4 germline gene (SEQ ID NO:37). Where the BAT sequence and the germline sequence are identical the germline sequence is represented by a dot (.); where mismatches occur the different germline residue is shown. The tables below and on the following pages describe the frequency with which certain amino acids have been seen at a particular residue position both within the Kabat mouse heavy chain subgroup VI (Mouse $V_K$ VI) and across a larger database of all known mouse $V_K$ sequences (All Mouse $V_K$);

FIG. 5 shows the DNA (SEQ ID NO:5) and peptide (SEQ ID NO:6) sequences of the Kappa light chain variable regions of the chimeric antibody of the invention;

FIG. 6 shows the DNA (SEQ ID NO:7) and peptide (SEQ ID NO:8) sequences of the heavy chain variable region of the chimeric antibody of the invention;

FIG. 10 shows the amino acid sequence of peptide 1 (SEQ ID NO:9) of the invention.

FIG. 11 shows the amino acid sequence of peptide 2 (SEQ ID NO:10) of the invention.

FIG. 12 shows the amino acid sequence of peptide 3 (SEQ ID NO:11) of the invention.

I. SEQUENCING OF THE MAB

(A) Abbreviations

Figure 7:
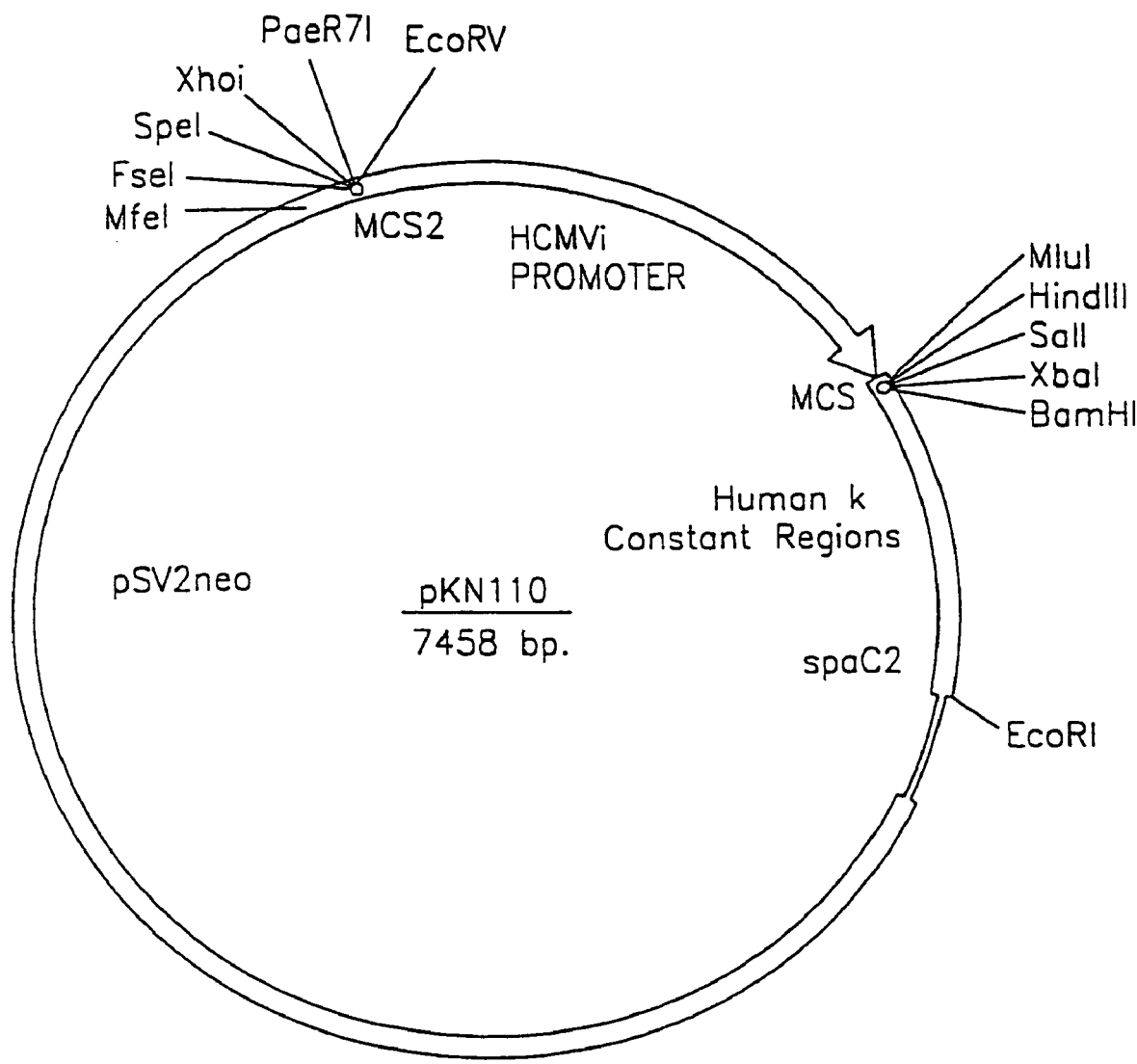
FIG. 7 shows a schematic representation of the pKN 110 mammalian expression vector used for the expression of the Kappa light chain of the chimeric antibody of the invention.

Fetal Calf Serum (FCS); ribonucleic acid (RNA); messenger RNA (mRNA); deoxyribonucleic acid (DNA); copy DNA (cDNA); polymerase chain reaction (PCR); minute (min); second (sec); Tris-borate buffer (TBE).

(B) Materials

Media components and all other tissue culture materials were obtained from Life Technologies (UK). The RNA isolation kit was obtained from Stratagene (USA) while the 1$^{st}$ strand cDNA synthesis kit was purchased from Pharmacia (UK). All the constituents and equipment for the PCR-reactions, including AMPLITAQ® DNA polymerase, were purchased from Perkin Elmer (USA). The TA CLONING® kit was obtained from Invitrogen (USA). Agarose (UltraPure™) was obtained from Life Technologies (UK). The THERMO SEQUENCES™ pre-mixed cycle sequencing kit and the Vistra 725 DNA sequencing machine were both purchased from Amersham (UK). All other molecular biological products were obtained from New England Biolabs (USA).

(C) Experimental Techniques

PCR Cloning and Sequencing of the Mouse BAT Antibody Variable Region Genes

The mouse BAT hybridoma cell line and the Daudi cell line were successfully transferred to the MRC-CC and both cell lines were grown, in suspension, using RPMI (without glutamine) supplemented with 10% (v/v) FCS, 100 units/ml penicillin, 100 µg/ml streptomycin and 2 mM L-glutamine, 1 mM sodium pyruvate and 12.5 units/ml Nystatin.

Approximately 10⁸ of viable cells of the BAT hybridoma cell line were harvested and, from the 10⁸ cells, total RNA was isolated using an RNA Isolation kit according to the manufacturers instructions. The kit used a guanidinium thiocyanate phenol-chloroform single step extraction procedure as described by Chromczynski and Sacchi, *Anal. Biochem.*, 162:156, 1987. Also following the manufacturers instructions a $1^{st}$ Strand cDNA synthesis kit was employed to produce a single-stranded DNA copy of the BAT hybridoma mRNA using the NotI-(dT)$_{18}$ primer supplied in the kit. Approximately 5 µg of total RNA was used in each 33 µl final reaction volume. The completed reaction mix was then heated to 90° C. for 5 min. to denature the RNA-cDNA duplex and inactivate the reverse transcriptase, before being chilled on ice.

To PCR-amplify the mouse heavy chain variable region gene ($V_H$ gene) and the mouse kappa light chain variable region gene ($V_\kappa$ gene) from the hybridoma cell line the method described by Jones and Bendig, *Bio/Technology*, 9:8, 1987 was followed. Essentially, two series of degenerate primers, one designed to anneal to the leader sequences of the mouse heavy chain genes (i.e. MHV1-12; Table 1) and one designed to anneal to the leader sequences of mouse kappa light chain genes (i.e. MKV1-11; Table 2) were used, in conjunction with primers designed to anneal to the 5'-end of the appropriate constant region gene, to PCR-clone the murine variable region genes.

Separate PCR-reactions were prepared for each of the degenerate primers with their appropriate constant region primer, in a special PCR-room using specific protocols designed to minimize the possibility of cross-contamination. AMPLITAQ® DNA polymerase was used to amplify the template cDNA in all cases. The PCR-reaction tubes were than loaded into a Perkin Elmer 480 DNA thermal cycler and cycled (after an initial melt at 94° C. for 1.5 min) at 94° C. for 1 min and 72° C. for 1 min over 25 cycles. At the completion of the last cycle a final extension step at 72° C. for 10 min was carried out before the reactions were cooled to 4° C. Except for between the annealing (50° C.) and extension (72° C.) steps, when an extended ramp time of 2.5 min was used, a 30 sec ramp time between each step of the cycle was employed.

10 µl aliquots from each PCR-reaction were run on a 1% agarose/TBE (pH 8.8) gel to determine which had produced a PCR-product of the correct size. Those PCR-reactions that did appear to amplify full-length variable region genes were repeated to produce independent PCR-clones and thereby minimize the effect of PCR-errors. 1-6 µl aliquots of those PCR-products of the correct size were directly cloned into the PCRII™ vector, provided by the TA CLONING® kit, and transformed into INA αF' competent cells as described in the manufacturers instructions. Colonies containing the plasmid, with a correctly sized insert, were identified by PCR-screening the colonies using the pCRII Forward and pCRII Reverse oligonucleotide primers described in Table 3 below according to the method of Güssow and Clackson, *Nucleic Acids Res.*, 17:4000, 1989

Those putative positive clones identified were double-stranded plasmid DNA sequenced using the Vistra DNA sequencing machine and the THERMO SEQUENASE™ pre-mixed cycle sequencing kit as described in the manufacturers instructions.

Example 1

Cloning and Sequencing of the Heavy Chain Variable Region of the BAT Antibody

As with all humanization projects, a strict PCT-cloning and sequencing protocol was followed. This was done to minimize the possibility of introducing errors into the wild-type sequences of the mouse $V_H$ variable region genes from the BAT hybridoma cell line. Only if all the DNA sequence data from at least two different $V_H$ gene clones, from the hybridoma cell line expressing the murine BAT antibody, matched perfectly were the gene sequences accepted as correct.

Three separate PCR-products, each from a different total RNA preparation and subsequent first strand cDNA synthesis reaction, were PCR-cloned and completely DNA sequenced on both strands. Although all twelve heavy chain primers were tested (Table 1), only the MHV9 primer (in conjunction with MHCG3—designed to anneal to the $CH_1$ domain of the mouse γ3 heavy chain gene) was PCR-amplified an approximately 460 bp product which was then TA-cloned into the PCRII™ cloning vector (data not shown).

DNA sequence analysis of several individual clones from each of the three PCR-products (each from different $1^{st}$ strand synthesis reactions and subsequent PCR-reactions) resulted in the determination of the BAT antibody heavy chain variable region sequence as described in FIG. 1. This sequence was confirmed on both DNA strands for all three PCR-clones studied.

Example 2

Cloning and Sequencing of the Kappa Light Chain Variable Region of the BAT Antibody The single stranded cDNA template, produced via $1^{st}$ strand synthesis, was PCR-amplified using a series of kappa light chain degenerate primers (Table 2 below). However, this resulted in the amplification of a number of PCR-products from more than one degenerate primer, suggesting that more than one variable region gene was being transcribed, at least, by the BAT hybridoma cell line.

First, a PCR-product was seen when the MKV2 primer (which, like all of the MKV series of primers, anneals to the 5' end of the DNA sequence of the kappa light chain signal peptide) and MKC (which is designed to anneal to the 5' end of the mouse kappa constant region gene) were used together. Previous in-house experience had shown us that the MKV2 primer would PCT-amplify an aberrant mRNA transcript. This aberrant pseudogene was present in all standard fusion partners derived from the original MOPC-21 plasmacytoma cell line and was known as MOPC-21n Deyev, S. M., et al., *Genetica*, 85:45, 1991. NO-0 was a cell line which was derived from MOPC-21 line, and it was this line which was used as the fusion partner to produce the BAT hybridoma. Consequently, it was not surprising that a PCR-product was seen when using the MKV2 primer. This product was analyzed and shown to be the non-functional pseudogene (data not shown).

Unusually, another pseudogene, previously identified as being secreted by the related cell line NS-1 Hamlyn, P. H., et al., *Nucl. Acis Res.*, 9:4485, 1981 and normally PCR-cloned when using the MKV7 primer in conjunction with MKC primer, was not seen in any of the PCR-products so far analyzed. Since the NS-1 and NS-0 cell lines were very closely related, this was a little surprising. However, it also highlighted the confusing nature of kappa light chain transcription that was present in the BAT hybridoma cell line.

Another PCR-clone, which ultimately turned out to be the $V_K$ gene of the BAT antibody, was also successfully PCR-amplified from the BAT hybridoma cell line with the primers MKV5 and MKC. Following transformation of the approximately 450 bp product into INVαF' competent cells, putative positive transformants were identified using the PCR-screening assay and then DNA sequenced.

From sequence analysis of two individual clones of the MKV5 product (each from different 1$^{st}$ strand synthesis reactions and subsequent PCR-reactions) the DNA sequence of the BAT antibody kappa light chain variable region gene was determined (FIG. 2). This sequence was again confirmed on both DNA strands for each clone.

Example 3

Sequence Analysis of the Mouse BAT Antibody Variable Regions

The amino acid sequence of the BAT $V_K$ and $V_H$ regions were compared to the consensus sequences of murine variable region subgroups that were defined in the Kabat (Supra) database From this analysis the BAT $V_H$ region was found to most closely match the consensus sequence of mouse kappa subgroup VI. Similar comparisons of the BAT $V_H$ region to the Kabat database found that it exhibited the closest match to the consensus sequence of mouse heavy chain subgroup "miscellaneous".

A comparison of the above BAT antibody variable region sequences to a database of murine germlines, found that the closest germline gene to the BAT $V_H$ gene was VMS/VGK4 (FIG. 3), whilst the closest germline gene to the BAT $V_K$ gene was H4 (FIG. 4). As can be seen in FIG. 3, those mismatches that did occur between the BAT $V_H$ gene and its closest germline gene were, unsurprisingly, predominantly located in the CDR2 and CDR3. There were only three framework changes, and all these were located in FR3. With respect to the BAT $V_K$ gene (FIG. 4), it was again not all together surprising that the majority of mismatches were positioned in the CDRs. The four differences that were located in the FRs were all highly conservative changes, except for the cysteine at position 72 (Kabat numbering) in FR3. Its location immediately adjacent to an important canonical residue (position 71) suggested that the cysteine may have been playing a key role in antigen binding. However, only through modeling the Fv domain could such a supposition be clarified.

Nevertheless, these analyses confirmed that both the $V_H$ regions and the $V_K$ regions of the mouse BAT variable regions appeared to be typical of mouse variable regions.

TABLE 1

PCR-primers used in the cloning of the BAT heavy chain variable region gene

| Name | SEQ ID NO. | Sequence (5' → 3') |
| --- | --- | --- |
| MHV5[a] (30 mer) | 12 | ATGGACTCCAGGCTCAATTTAGTTTTCCTT |
| MHV9[a] (30 mer) | 13 | ATGGATTGGGTGTGGACCTTGCTATTCCTG C A |
| MHCG3[b] (21 mer) | 14 | ———CAAGGGATAGACAGATGGGGC |

[a]MHV indicates a primer that hybridizes to leader sequences of mouse heavy chain variable region genes.
[b]MHCG indicates primers that hybridize to mouse constant region genes.

TABLE 2

PCR-primers used in the cloning of the BAT kappa light chain variable region gene

| Name | SEQ ID NO. | Sequence (5' → 3') |
| --- | --- | --- |
| MKV2[a] (30 mer) | 15 | ATGGAGACAGACACACTCCTGCTATGGGTG T T |
| MKV5[a] (30 mer) | 16 | ATGGATTTTCAGGTGCAGATTATCAGCTTC A T |
| MKV6[a] (30 mer) | 17 | ATGAGGTGCCCTGTTCAGTTCCTGGGG T TT C G C T A |
| MKV11[a] (30 mer) | 18 | ATGGAAGCCCCAGCTCAGCTTCTCTTCC |
| MKC[b] (20 mer) | 19 | ACTGGATGGTGGGAAGATGG |

[a]MKV indicates primers that hybridize to leader sequences of mouse kappa light chain cariable region genes
[b]MKC indicates the primer that hybridizes to the mouse kappa constant region gene

TABLE 3

Primers for PCR screening transformed colonies

| Name | SEQ ID NO | Sequence (5' → 3') |
| --- | --- | --- |
| pCRII Forward Primer (18 mer) | 20 | C T A G A T G C A T G C T C G A G C |
| pCRII Reverse Primer (21 mer) | 21 | T A C C G A G C T C G G A T C C A C T A G |

II. CONSTRUCTION AND EXPRESSION OF THE CHIMERIC ANTIBODY OF THE INVENTION

(A) Abbreviations

The following non-SI unit and other abbreviations were used:

Polymerase chain reaction (PCR); deoxyribonucleic acid (DNA); copy DNA (cDNA); kappa light chain variable region ($V_\kappa$); heavy chain variable region ($V_H$); minute (min); Tris-borate buffer (TBE); phosphate buffered saline (PBS); room temperature (RT), bovine serum albumin (BSA); hydrochloric acid (HCl); horseradish peroxidase (HRP); low fat milk LFM); hour (hr); percent (%); O-phenylenediamine dihydrochloride (OPD); multiple cloning site (MCS).

(B) Materials

Media components and all other tissue culture materials were obtained from Life Technologies (UK). The constituents for the PCR-reactions, including AMPLITAQ® DNA polymerase, were purchased from Perkin Elmer (USA). However, the TA CLONING® kit and INVαF' competent cells were obtained from Invitrogen (USA). DH5α competent cells and agarose (ULTRAPURE™) were obtained from Life Technologies (UK). The THERMO SEQUENASE™ pre-mixed cycle sequencing kit and the Vistra 725 DNA sequencing machine were both purchased from Amersham (UK). The BIG DYE™ Terminator Cycle Sequencing Ready Reaction Kit used with the ABI Prism 310 Genetic Analyzer were purchased from PE Applied Biosystems (UK). All other molecular biological products described were obtained either from New England biolabs (USA) or Promega (USA). Nunc-Immuno Plate MAXISORP™ immunoplates were purchased from Life Technologies (UK) while the Corning easy wash ELISA plates were obtained from Corning Laboratory Sciences Company (UK). The goat anti-human IgG ($Fc_\gamma$ fragment specific) antibody, the goat anti-human kappa light chain/HRP conjugate and the AffinPure goat anti-human IgG ($Fc_\gamma$ fragment specific)/HRP conjugate were obtained from Jackson ImmunoResearch Laboratories Inc. (USA). K-Blue TMB substrate and Red Stop solution were purchased from Neogen Inc. (USA). All other products for the ELISA were obtained from Sigma (UK). MICROPLATE MANAGER® data analysis software package was purchased from Bio-Rad (UK). The micro-volume stirred ultrafiltration cell and PM30 filter membrane were obtained from Amicon PLC (UK), while the IMMUNOPURE® (G) IgG purification kit was purchased from Pierce PLC (UK).

(C) Experimental Techniques

C1 Construction of Chimeric γ1/κ BAT Antibody

The previously isolated mouse kappa light chain variable region ($V_\kappa$) gene (FIG. 1) and heavy chain variable region ($V_H$) gene (FIG. 2) were modified at the 5'- and 3'-ends, using specifically designed PCR-primers (Table 1), to enable expression of the BAT variable region genes in mammalian cells as part of a chimeric mouse-human antibody. To achieve this separation PCR-reactions were prepared for each variable region gene in a specific PCR-room using specific protocols designed to minimize the possibility of cross-contamination. The plasmids $BATV_H$-pCR2.1 and $BATV_\kappa$-pCR2.1 were used as templates and AMPLITAQ® DNA polymerase was used t amplify these templates. Primers B8814 and B8815 (Table 4) were used to PCR-modify the BAT $V_H$ gene while primers C0224 and C0225 (Table 4) were used to PCR-mutate the BAT $V_\kappa$ gene.

The PCR-reaction tubes were cycled (after an initial melt at 94° C. for 3 min) at 94° C. for 50 s, 72° C. for 1 min 30 s over 30 cycles. At the completion of the last cycle a final extension step at 72° C. for 10 min was carried out before the reactions were cooled on ice. 5 µl aliquots from each PCR-reaction were then run on a 1.2% agarose/TBE (pH 8.8) gel to determine which had produced a PCR-product of the correct size.

1-2 µl aliquots of those PCR-products of the correct size were directly cloned into the pCR2.1™ vector, provided by the TA CLONING® kit, and transformed into INVαF' competent cells as described in the manufacturers instructions. Colonies containing the plasmid, with a correctly sized insert, were identified by PCR-screening the colonies using the 1212 and 1233 oligonucleotide primers (Table 5) according to the method of Güssow and Clackson (Supra) Those putative positive clones identified were double-stranded plasmid DNA sequenced using both the Vistra DNA sequencing machine and ABI Prism 310 Genetic Analyzer. The THERMO SEQUENASE™ pre-mixed cycle sequencing kit and the BIG DYE™ Terminator Cycle Sequencing Ready Reaction Kit were used as described in the manufacturers instructions with the primers 1212 and 1233 (Table 5).

Figure 8:
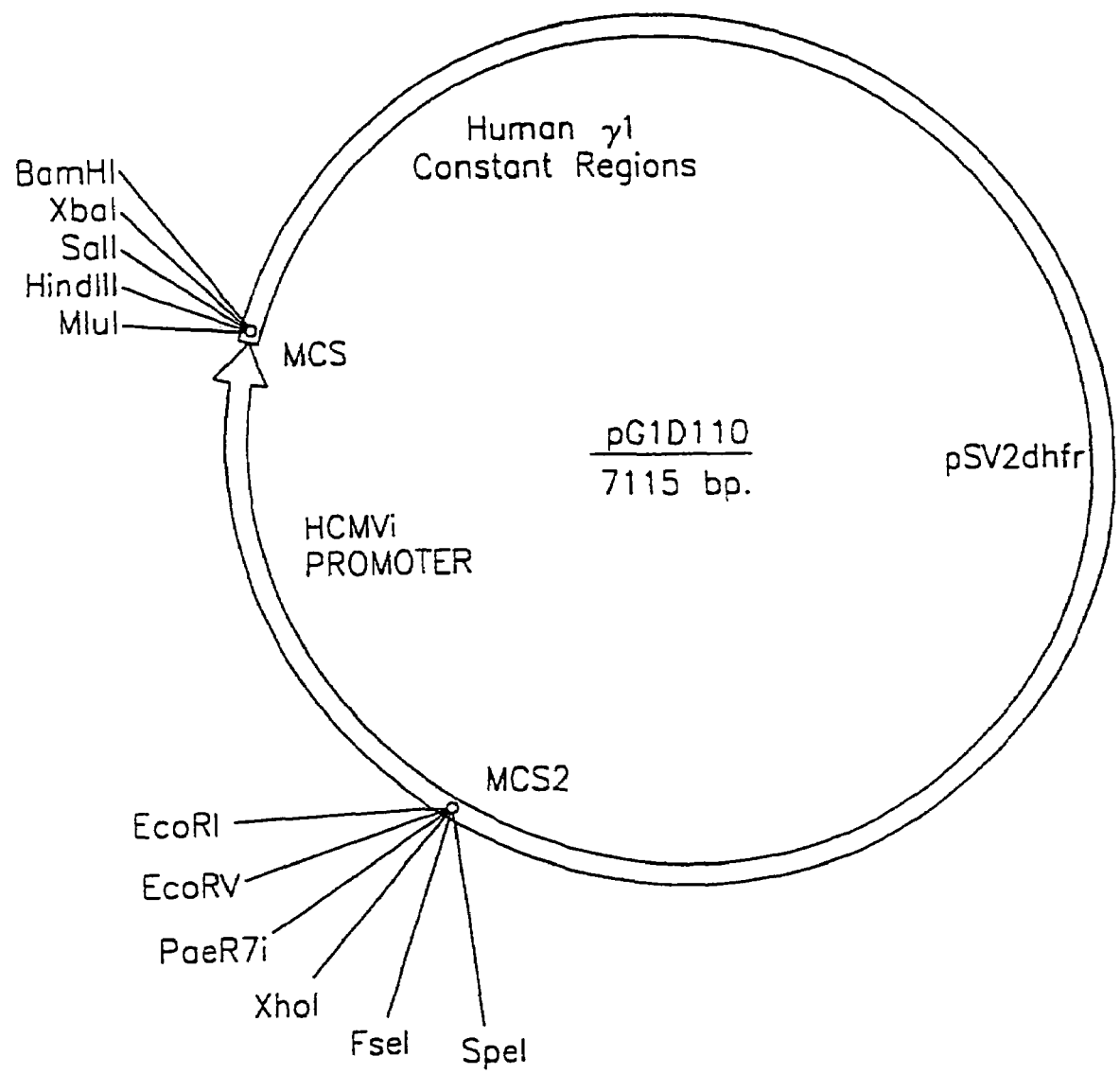
FIG. 8 shows a schematic representation of the pG1D 110 mammalian expression vector used for the expression of the heavy chain of the chimeric antibody of the invention.

Those clones containing the correctly adapted BAT $V_\kappa$ and $V_H$ genes (FIGS. 5 and 6, respectively) were subcloned, as a HindIII-BamHi fragments, into the expression vectors pKN110 (FIG. 7) and pG1D110 (FIG. 8), respectively, to express chimeric light and heavy chains in mammalian cells. The ligated expression vectors (i.e. pKN110-BATV$_\kappa$ and pG1D110-BATV$_H$) were then transformed into DH5α competent cells. Positive clones, containing the correctly constructed expression vectors, were finally identified by restriction digest analysis.

C2 Co-Transfection of Chimeric γ1/κ BAT Antibody Vector DNA into COS Cells

The method of Kettleborough et al. was followed to transfect the mammalian expression vectors into COS cells. Briefly, the DNA (10 µg each of the kappa light chain expression vector pKN110-BATV$_\kappa$ and heavy chain expression vector pG1D110-BATV$_H$) was added to a 0.70 ml aliquot of $1 \times 10^7$ cells/ml in PBS and pulsed at 1900 V, 25 µF capacitance using a Bio-Rad Cene Pulser apparatus. Following a 10 min recovery at RT the electroporated cells were added to 8 ml of DMEM containing 5% FCS and incubated for 72 hr in 5% $CO_2$ at 37° C. After 72 hr incubation, the medium was collected, spun to remove cell debris and analyzed by ELISA for chimeric BAT antibody production.

C3 Quantification of Chimeric γ1/κ Antibody Via ELISA

Each well of a 96-well Nunc-Immuno Plate MAXISORP™ immunoplate as first coated with 100 µl aliquots of 0.4 ng/µl goat anti-human IgG ($Fc_\gamma$ fragment specific) antibody, diluted in PBS and incubated overnight at 4° C. and removed prior to use. 100 µl/well aliquots f the experimental samples (i.e. harvested COS cell supernatants—spun to remove cell debris) and 1:2 sample dilutions, diluted in sample-enzyme conjugate buffer (0.1 M Tris-HCl (pH 7.0), 0.1 M NaCl, 0.02% (v/v) TWEEN-20 and 0.2% (w/v) BSA), were then dispensed onto the immunoplate. In addition, a purified human γ1/κ antibody (1000 ng/µl), which was used as a standard and serially diluted 1:2, and also loaded onto the immunoplate. The immunoplate was incubated at 37° C. for 1 hr before being washed with 200 µl/well of wash buffer (PBS/ 0.1% (v/v) TWEEN-20) three times. 100 µl of goat anti-human kappa light chain/horseradish peroxidase conjugate, diluted 5000-fold in sample-enzyme conjugate buffer, was added to each well, following which the immunoplate was incubated at 37° C. for 1 hr before it was washed as before. 150 µl aliquots of K-Blue substrate were then added to each well, following which the immunoplate was incubated for 10 min at RT in the dark. The reaction was finally halted by dispensing 50 µl of Red Stop into each well. The optical density at 655 nm was then determined using a Bio-Rad 3550 microplate reader in conjunction with the MICROPLATE MANAGER® software package.

C4 Purification of the Chimeric BAT Antibody

The chimeric BAT γ1/κ antibody was purified from COS cell supernatants in two stages. First, a micro-volume stirred ultrafiltration cell with a PM30 filter membrane was used, according to the manufacturers instructions, to reduce the volume of the raw, non-purified supernatant. Then an IMMU-NOPURE® (G) IgG purification kit was used to affinity purify the chimeric BAT antibody from the concentrated supernatant, also according to the manufacturers instructions.

C5 Daudi Cell ELISA

The cell ELISA assay was carried out using the Daudi cell cultured from an original stock also by Dr. Hardy (Felsenstein Medical Research Center, Rabin Medical Center, Beilinson Campus, Petach Tikva, 49100, Israel). Minor modifications were made to the assay depending upon whether the mouse or the mouse-human chimeric BAT antibody was being analyzed. When assaying the binding affinity of the mouse BAT antibody a goat anti-mouse IgG (Fab specific)/HRP conjugate (diluted 1:15000) was used as the secondary antibody. Conversely, when measuring the affinity of the chimeric BAT antibody AffiniPure goat anti-human IgG ($Fc_\gamma$ fragment specific)/HRP conjugate (diluted 1000-fold) was used.

The Daudi cells (2 days after being passaged) were first plated at $10^5$ cells/well in a 96 well Corning easy wash ELISA plate and then incubated overnight at 37° C. in a dry incubator. The next day, 200 µl of rehydration buffer (PBS containing 10% FCS and 0.05% azide) was added to each well which was then left for a minimum of 1 hr. The rehydration buffer was then decanted off before 50 µl aliquots of various 1:2 serial dilutions of the purified BAT antibody was added to the wells of the plate. The plate was again incubated overnight (at 4° C.), washed twice with 200 µl/well of PBS containing 5% LFM and allowed to dry. 50 µl/well of the HRP conjugated secondary antibody was then added before a series of six different washes (i.e. one wash with PBS containing 5% LFM, three washed with the same buffer supplemented with 0.05% TWEEN-20, followed by a further two washes with the PBS/LFM buffer) were carried out. 200 µl/well of 0.4 mg/ml OPD substrate in 0.05 M citrate buffer (pH 5.0) and 60 mg/ml hydrogen peroxide was then added before the ELISA plate was incubated in the dark and at RT until the color had developed (usually about 30 min). Finally, the reaction was stopped by the addition of 50 µl/well of 2.5 M sulfuric acid and the optical density at 490 nm was then measured using a Bio-Rad 3550 microplate reader in conjunction with the Microplate Manager® software package.

Results

Example 4

Construction of the Chimeric γ1/κ BAT Antibody

As with all projects, a strict PCR-cloning and sequencing protocol was followed. This was done to minimize the possibility of introducing errors into the wild-type sequences of the mouse variable region genes during the PCR-modification step. Using the primers C0224 and C0225 (Table 1) the mouse BAT $V_\kappa$ gene (FIG. 2) was modified via PCR to produce a 418 bp band (data not shown). This PCR-product was ligated into the pCR2.1 plasmid and transformed into INVαF' competent cells. Similarly, the mouse BAT $V_H$ gene (FIG. 1 was PCR-mutated using primers B8814 and B8815 (Table 1) to produce a 436 bp band (data not shown). This PCR-product was also ligated into the pCR2.1 plasmid and transformed into INVαF' competent cells.

Putative positive transformants were then detected using the PCR-screening assay (data not shown) before finally being ds-DNA sequenced on the ABI Prism 310 Genetic Analyzer. FIGS. 3 and 4 show the results of this DNA sequence analysis of the chimeric BAT $V_\kappa$ gene and BAT $V_H$ gene, respectively. The analysis was carried out both to confirm their successful mutagenesis and also show the presence of any PCR-errors that may have been introduced into the genes. Only one PCR-reaction was actually carried out for each variable region gene and only two clones from each of these PCR-reactions were eventually DNA sequences to completed.

Nevertheless, this proved sufficient to isolate at least one clone for each modified variable region gene which contained the correct modified DNA sequence.

The mutated $V_H$ and $V_\kappa$ genes were then subcloned into the appropriate expression vectors, as hindIII/BamHI fragments, to create pKN110-BATV$_\kappa$ (7.88 kb) and pG1D110-BATV$_H$ (7.55 kb), respectively. The fidelity of the expression vectors constructed was then confirmed via restriction enzyme analysis (data not shown). Once co-transfected into COS cells, these vectors wold allow the transient expression of a γ1/κ version of the chimeric BAT antibody.

In addition, as an extra component to the BAT antibody humanization project, the BAT $V_H$ gene was also subcloned, as a HindIII/BamHI fragment, into both the pG3D110 and the pG4D1100 heavy chain expression vectors. These vectors were identical to pG1D110, save for the replacement of the cDNA copy γ1 human constant region genes with either a cDNA copy of the 3γ constant region genes (in the case of pG3D110) or the cDNA of the γ3 constant region genes (in the case of pG3D110) or the cDNA of the γ4 constant region genes (in the case of pG3D110). The construction of these vectors (i.e. pG3D110-BATV$_\kappa$, of both γ3/$_\kappa$ and γ4$_\kappa$ versions of the chimeric BAT antibody in COS cells.

Example 5

Transient Expression of the Chimeric γ1/κ0 BAT Antibody

The two vectors pKN110-BATV$_\kappa$ and pG1D110-BATV$_H$ were co-transfected into COS cells in a series of repeated transient expression experiments. After being expressed for 72 hr the mouse-human γ1/$_\kappa$ chimeric BAT antibody was detected in the supernatant of the COS cell co-transfections via the γ1/$_\kappa$ ELISA. From these assays the mean concentration of γ1/$_\kappa$ chimeric BAT antibody detected in the media was calculated to be 509±272 ng/ml.

Interestingly, the γ3/$_\kappa$ and γ4/$_\kappa$ versions of the chimeric BAT antibody appeared to produce significantly greater quantities of antibody following their expression COS cells. Specifically, when pG3D110-BATV$_H$ and pKN110BATV$_\kappa$ were co-transfected into COS cells, initial analysis of the supernatant (using the ELISA method described in Section 4.3 and human IgG3/kappa antibody as a standard) measured the expression levels of the chimeric γ3/$_\kappa$ BAT antibody to be 6.7 µg/ml. Moreover, when pG4D110-BATV$_H$ pKN110-

BATV$_\kappa$ were expressed in COS cells, the same ELISA (using human IgG4/kappa antibody as a standard) measured the expression levels of the chimeric γ4/$_\kappa$ BAT antibody to be 8.2 µg/ml.

Example 6

Purification of the Chimeric γ1/$_\kappa$ BAT Antibody

Harvesting approximately 8 ml per co-transfection, a series of transfections were carried out until 200 ml of COS supernatant had been collected. The volume of this supernatant was then reduced to 15 ml by passing the supernatant through a micro-volume stirred ultrafiltration cell with a PM30 filter membrane—which had a molecular weight cut-off of 30 kDa.

The IMMUNOPURE® (G) IgG purification kit essentially comprised of a 2 ml column of immobilized Protein G column. The antibody was eluted from the column with 6 ml of elution buffer, the eluate of which was collected in 1 ml fractions. The concentration of chimeric γ1/$_\kappa$ BAT antibody in each fraction was then assayed using the ELISA method described in Section C3. This analysis found that the chimeric antibody was present in Fraction 3 (42.05 µg/ml) and Fraction 4 (20.05 µg/ml), which correspond to a total recovery of 62.1 µg of chimeric γ1/$_\kappa$ BAT antibody. This was stored at −20° C., until its subsequent transfer to Curetech for further analysis.

Example 7

Analysis of Daudi Cell Binding by the Chimeric γ1/$_\kappa$ Bat Antibody

Figure 9:
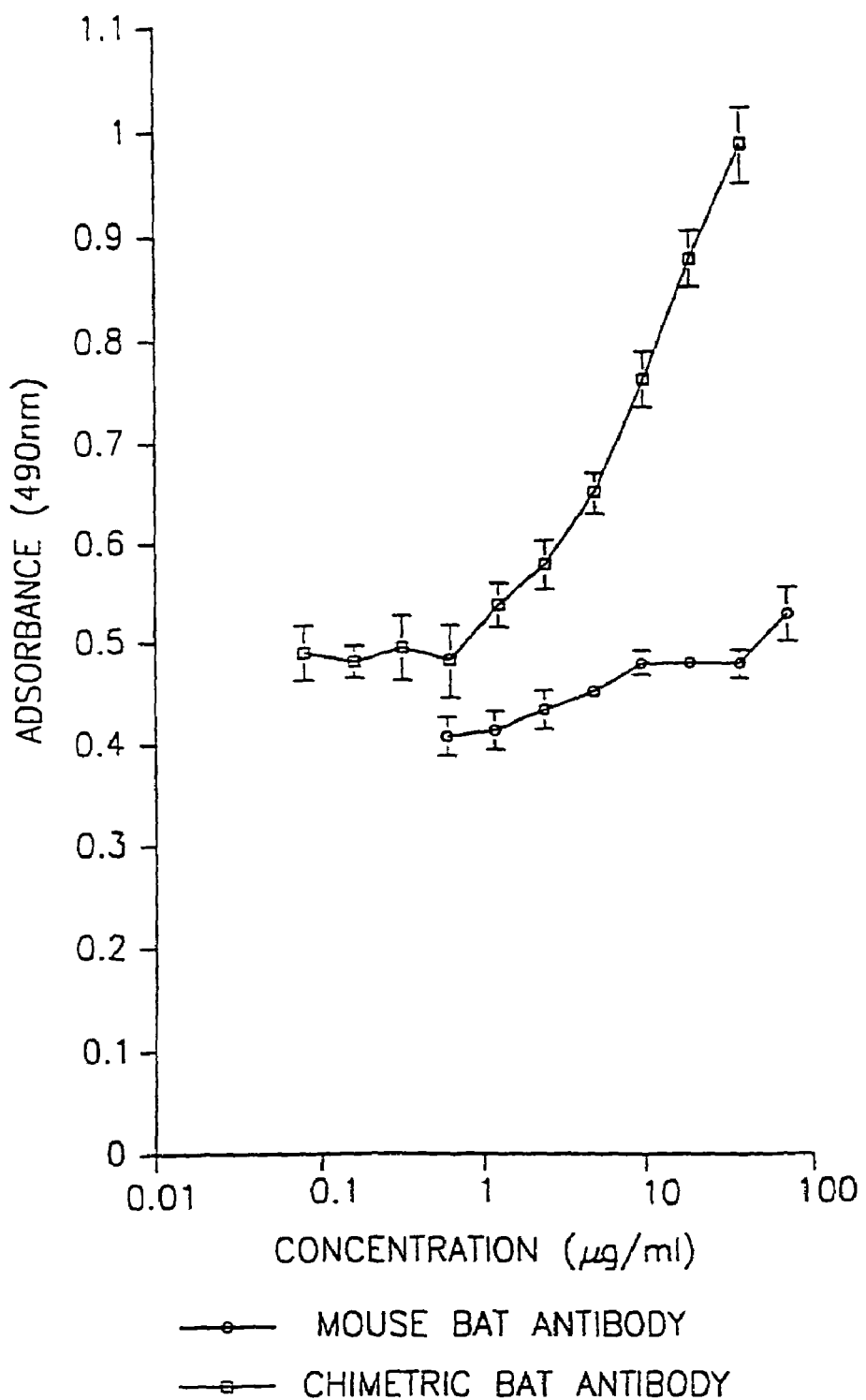
FIG. 9 shows a graphic representation featuring an example of results of an ELISA assay measuring the binding characteristics of the mouse and the γ1/Kappa chimeric antibody of the invention to Daudi cells.

Using the Daudi cell ELISA it was clearly shown that the purified chimeric γ1/$_\kappa$ BAT antibody bound to Daudi cells. FIG. 9 shows a typical example of one experiment. However, what was less conclusive was the binding of similar concentrations of mouse BAT antibody, in the same ELISA, which appeared to be lower than the chimeric antibody. Nevertheless, since the conjugated secondary antibody used to detect antibody binding to the Daudi cells was different for each antibody construct, no direct comparison of the binding of the two versions can legitimately be made.

TABLE 4

Primers used to PCR-modify the mouse BAT antibody kappa light chain and heavy chain variable region genes to allow their expression as part of a chimeric γ1/$_\kappa$ BAT antibody in mammalian cells

| Name | SEQ ID NO. | Sequence (5' → 3') |
|---|---|---|
| C0225 (42 mer) | 22 | CCCAAGCTTGCCGCCACCATG GATTTTCAGGTGCAGATTATC |
| C0224 (39 mer) | 23 | CGCGGATCCACTCACGTTTTA TTTCCAACTTTGTCCCCG |
| B8815 (40 mer) | 24 | GGATCCACTCACCTGAGGAGA CGGTGACTGAGGTTCCTTG |
| B8814 (42 mer) | 25 | AAGCTTGCCGCCACCATGGCT TGGGTGTGGACCTTGCTATTC |

TABLE 5

Primers used to PCR screen the transformed colonies and DNA sequence the PCR-modified variable region genes of the BAT antibody

| Name | SEQ ID NO. | Sequence (5' → 3') |
|---|---|---|
| Huγ1 (17 mer) | 26 | TTGGAGGAGGGTGCCAG |
| HCMVi.3s (28 mer) | 27 | GTCACCGTCCTTGACACGCGT CTCGGGA |
| FOR (18 mer) | 28 | TGTAAAACGACGGCCAGT |
| REV (18 mer) | 29 | GAAACAGCTATGACCATG |
| B6990 (27 mer) | 30 | CAGCATATGTTGACTCTCCAC TGTCGG |
| B6991 (27 mer) | 31 | GTCAACATATGCTGAAGAGTT CAAGGG |
| B8809 (18 mer) | 32 | TGCCAGGTCAAGTGTAAG |
| B8810 (18 mer) | 33 | AAGCCAGGTTGGATGTCC |

IV AMINO ACID SEQUENCES OF 3 PEPTIDES TAKEN FROM THE DAUDI B-CELL LYMPHOBLASTOID CELL LINE ANTIGEN TO WHICH THE MABS OF THE INVENTION BIND

Three peptides comprised in the antigenic epitope of the Daudi B lymphoblastoid cells to which the mAbs of the invention bind were sequenced. Their sequence depicted in FIGS. 10, 11 and 12.

Searches performed against the non-redundant gene bank database and the EST Division yielded no hits when the three peptides were ran as queries using the TBLASTN algorithm (Version 2) with an EXPECT value of 10 and the matrix BLOSUM 62.

However, since the peptides are small peptides, they were submitted again at a higher EXPECT value to make the search less stringent. The filter was also unmasked for low complexity which can eliminate potentially confounding matches (e.g. hits against proline-rich regions or proly-A tails) from the blast reports, leaving regions whose blast statistics reflect the specificity of their pairwise alignment. The three peptides of the invention did not yield any hit with the gene bank and the EST division database even at a very low stringency.

Thus, in accordance with the above results, the three above peptides seem to be novel peptides.

V DIAGNOSIS OF MALIGNANT DISEASES IN PATIENTS USING THE MAB OF THE INVENTION

Peripheral blood lymphocytes from tested individuals were double-labeled using the anti-CD3 antibody and one of the mAbs of the invention. The percent of $CD3^+$ cells which bind the mAbs of the invention were determined. In accordance with the invention, it has been shown that the number of the $CD3^+$ $mAb^+$ cells in individuals having a malignant disease differs from the percent of these cells in blood samples obtained from healthy individuals. The fact that there exists a significant difference of the percent of the $CD3^+$ cells in the individuals having a malignant disease and whether the difference is above or below the percent of $CD3^+$ $mAb^+$ cells obtained from healthy individuals enables to determine at high probability whether the individual has a malignant disease as well as the specific kind of malignant disease which the tested individual may have.

Typically, human peripheral blood lymphocytes were obtained from 20 ml blood of either a healthy individual or from cancer patients by Ficoll Hypaque density centrifugation. The cells were washed and suspended in PBS containing 0.5% BSA and 0.05% as acid. The samples containing $0.5 \times 10^6$ cells were used for FACS analysis. First, the cells were incubated with a saturated amount of the mAb of the invention for 45 mins. at 0° C. followed by their incubation with an anti-mouse mAb conjugated to FITC for 30 mins. on ice. After two washes and centrifugation at 1200 rpm cells were incubated with an anti-human CD3 conjugated to PE antibodies for 30 mins. on ice. Following this incubation, the cells were washed twice and the sample is analyzed by a FACS scan (Bectan Dickinson). The results are shown in FIGS. 13 to 17.

Figure 13:
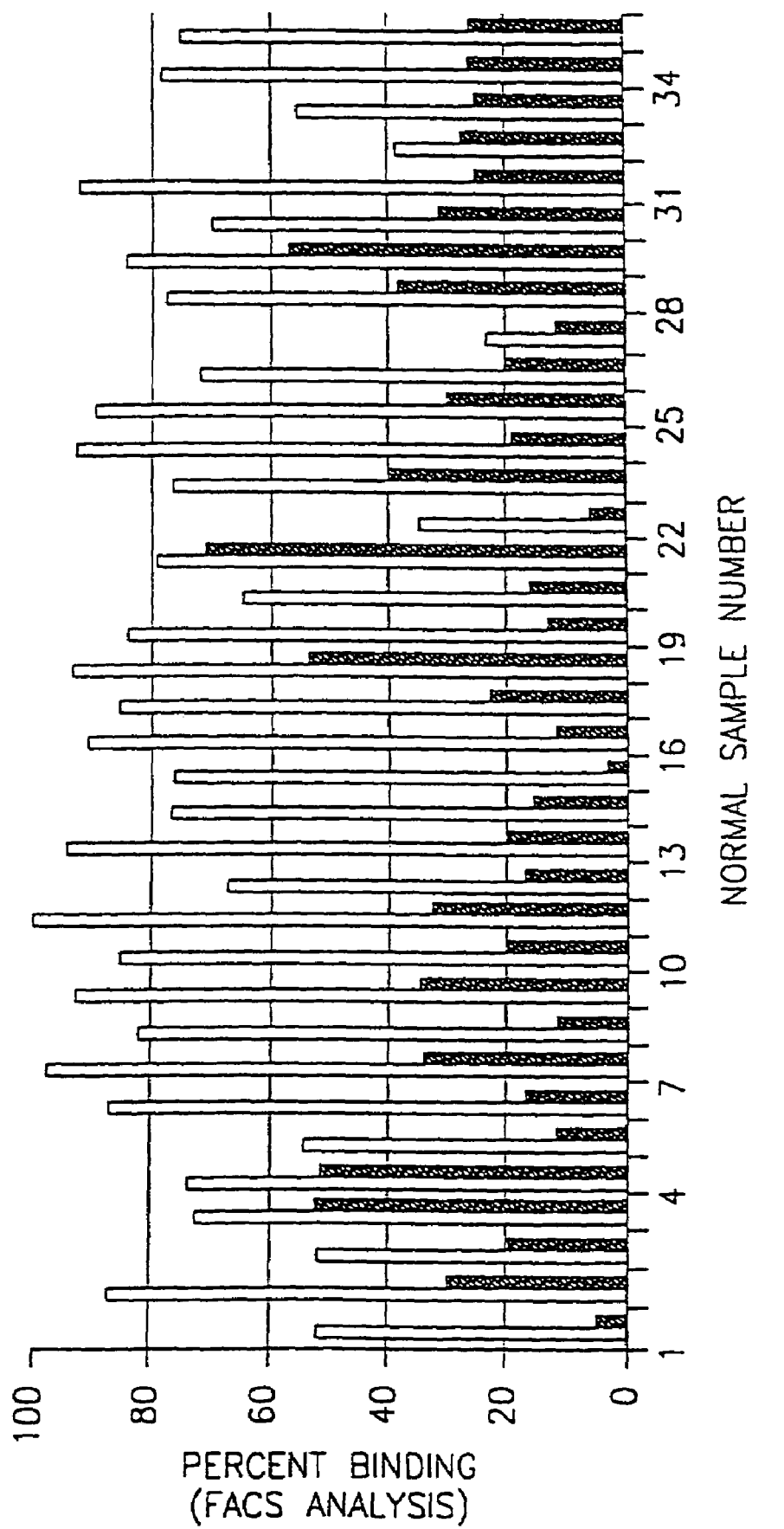
FIG. 13 is a schematical representation showing the percent of CD3+ cells which also bind the mAb of the invention (indicated as "BAT") as compared to the total number of CD3+ cells in blood samples of healthy individuals as determined by FACS analysis.
Figure 14:
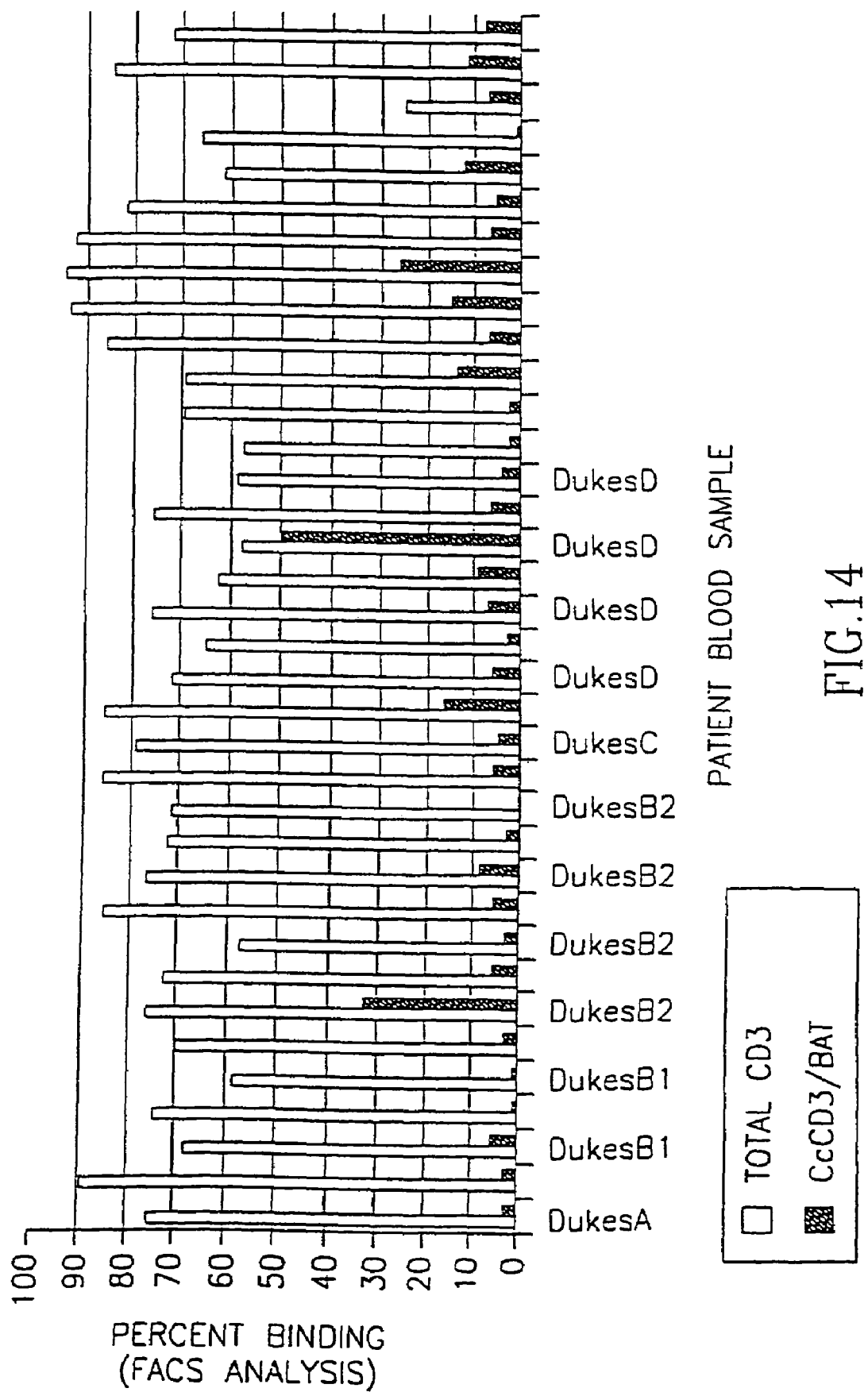
FIG. 14 shows the percent of CD3+ cells which also bind the mAb of the invention (indicated as BAT) as compared to the total number of CD3+ cells in blood samples taken from patients having colon carcinoma as determined by FACS analysis.
Figure 15:
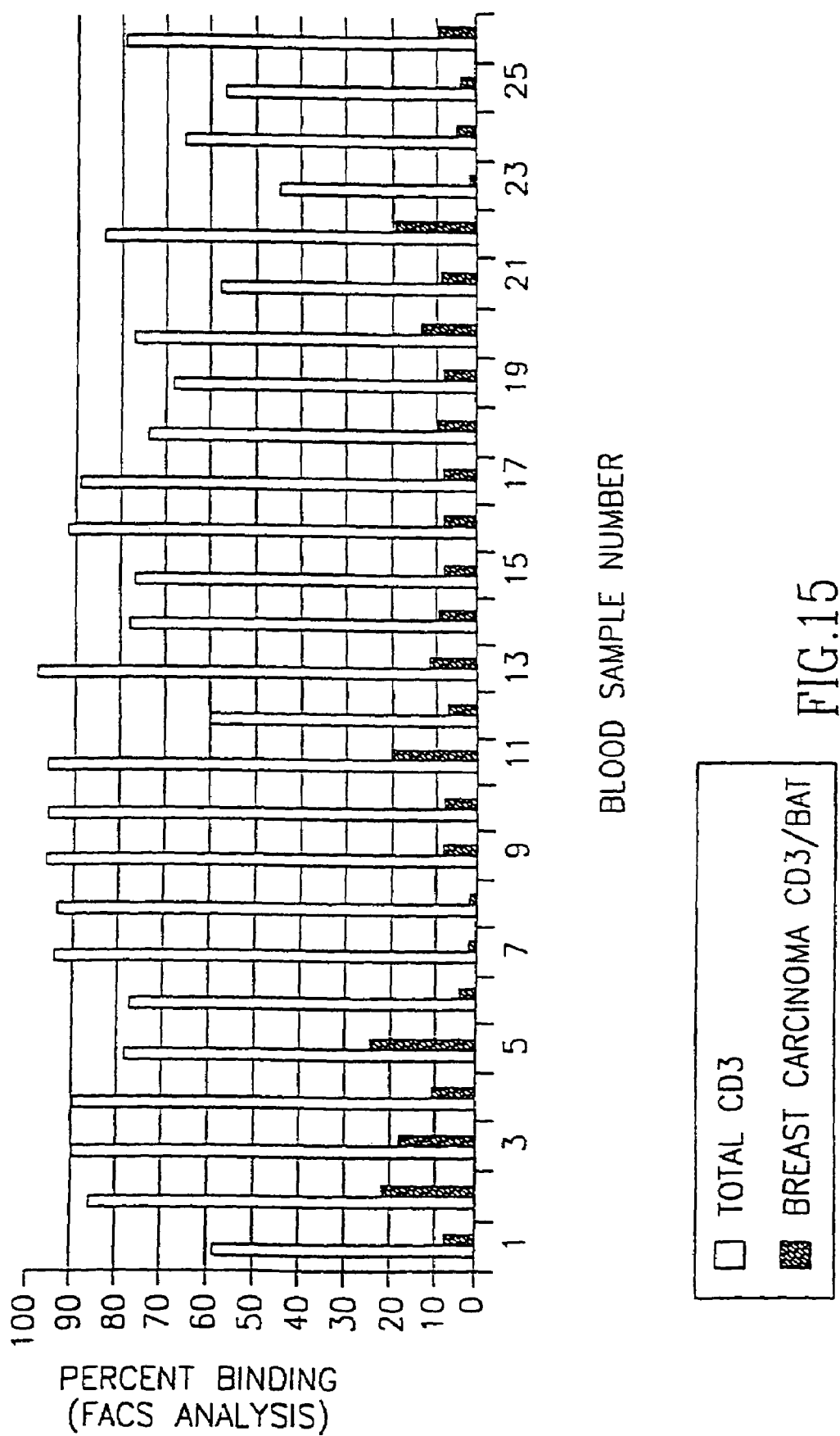
FIG. 15 shows the percent of CD3+ cells which also bind the mAb of the invention (indicated as BAT) as compared to the total number of CD3+ cells in blood samples obtained from patients having breast carcinoma.
Figure 17:
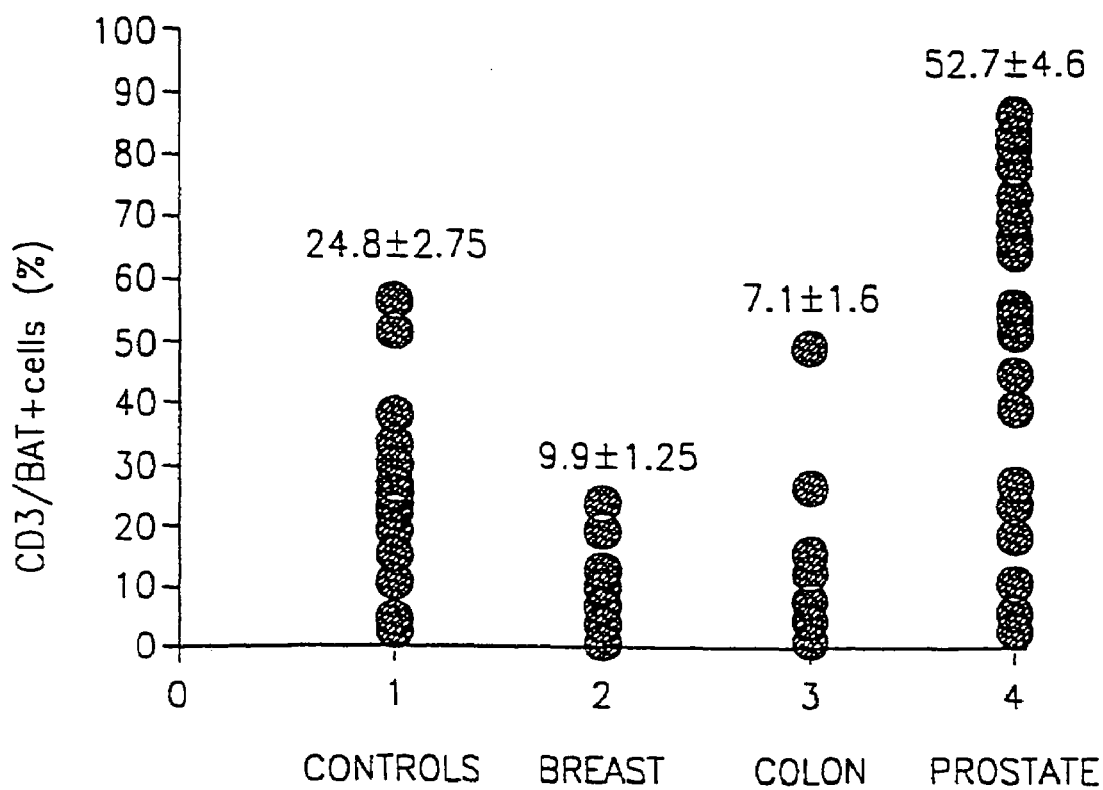
FIG. 17 is a schematic representation showing the mean percent of CD3+ cells which bind the mAb of the invention (indicated as BAT) in healthy individuals as compared to patients having breast carcinoma, colon carcinoma or prostate carcinoma.

As can be seen in FIG. 13, as well as in FIG. 17, the percent of $CD3^+$ $BAT^+$ cells (as compared to total $CD3^+$ cells) in blood samples obtained from healthy individuals is in the range of about 25%. As seen in FIG. 14, the percent of the $CD3^+$ $BAT^+$ cells in blood samples obtained from patients having colon carcinoma is substantively lower, as compared to healthy individuals, in the range of about 7%. Similarly, the percent of $CD3^+$ $BAT^+$ cells in blood samples obtained from patients having breast carcinoma was in the range of about 10% (FIG. 15). These results clearly indicate that colon and breast carcinoma can be identified by the fact that the percent of $CD3^+$ $BAT^+$ cells is lower as compared to healthy individuals.

Figure 16:
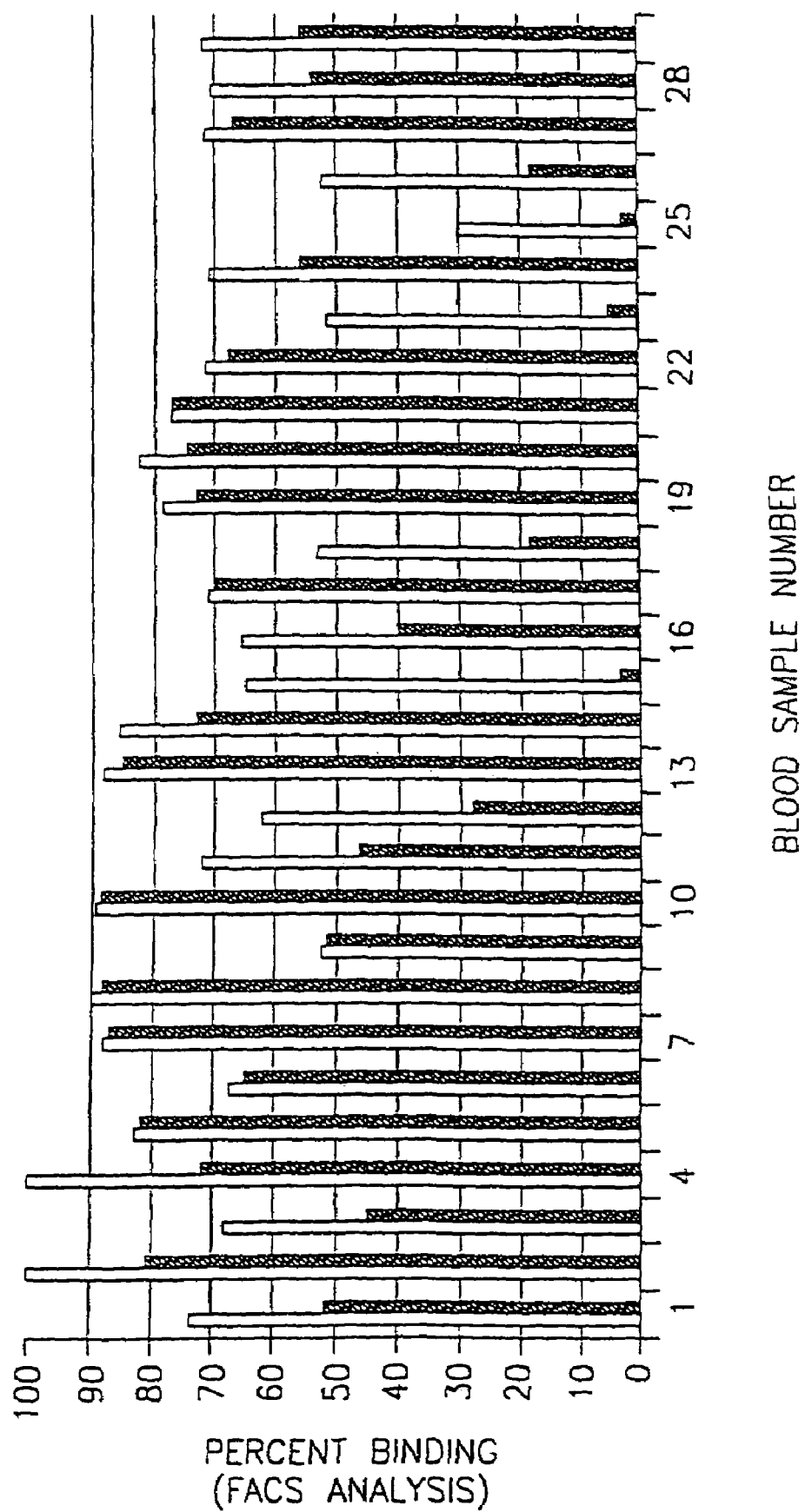
FIG. 16 shows the percent of CD3+ cells which also bind the mAb of the invention (indicated as BAT) as compared to the total number of CD3+ cells in blood samples obtained from patients having prostate carcinoma.
Figure 18:
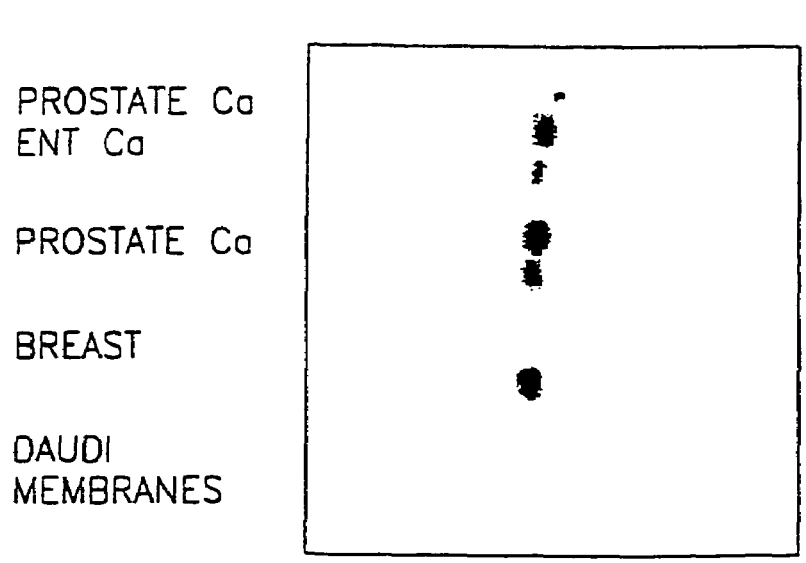
FIG. 18 is a photograph of a Western Blot of peptides obtained from T-cells of individuals having prostate cancer, ear, nose and throat (ENT) carcinoma, breast carcinoma or from membranes of Daudi cells. The Blot was incubated with the mAb of the invention and shows an increased amount of antigen in T-cells obtained from patients having prostate carcinoma as compared to an undetectable level of antigen in T-cells obtained from patients having breast carcinoma.

The percent of $CD3^+$ $BAT^+$ cells in blood samples obtained from prostate carcinoma patients is significantly higher than the percentage in blood samples of healthy individuals as seen in FIG. 16 and is in the range of about 50%. These results clearly indicate that prostate carcinoma can be identified by the fact that the percent of $CD3^+$ $BAT^+$ cells is higher a compared to healthy individuals. As seen in FIG. 18, the amount of the antigen to, which the mAb of the invention bind found on T-cells, obtained from prostate carcinoma patients is very high while the antigen is undetectable in T-cells obtained from patients of breast carcinoma.

The above results show that the mAbs of the invention may be used in order to identify an individual suffering from a certain kind of malignant disease. Thus, if a blood sample is obtained from a tested individual and the extent of binding of the mAbs of the invention to $CD3^+$ cells in the sample is significantly high (in the range of about 50%), there is a very high probability that the tested individual is suffering from prostate cancer. Against this, if the percent of the $CD3^+$ cells in the sample is significantly low as compared to healthy individuals (in the range of about 7% or 10%), there is a high probability that the tested individual is suffering from breast or colon carcinoma. Obviously, if the tested individual is a male individual, there is a high probability of his suffering from colon carcinoma.

The above examples are not to be construed as limiting and additional correlations between the percent of $CD3^+$ cells which bind the mAbs of the invention and other malignant diseases are also within the scope of the invention.

---

What is claimed is:

1. A method for the treatment of a malignant disease selected from the group consisting of prostate carcinoma and breast carcinoma, the method comprising administering to an individual in need thereof a therapeutically effective amount of a composition, wherein said composition comprises a monoclonal antibody comprising a heavy chain variable region consisting of the amino acids whose sequence is set forth in SEQ ID NO:2 and a light chain variable region consisting of the amino acids whose sequence is set forth in SEQ ID NO:4.

2. The method according to claim 1, wherein the monoclonal antibody is a chimeric human-mouse antibody.

3. The method of claim 1, wherein the monoclonal antibody is selected from the group consisting of IgG, IgM, IgD, IgA and IgE.

4. The method of claim 1, wherein the monoclonal antibody is a whole antibody.

5. The method of claim 1, wherein the monoclonal antibody is selected from the group consisting of an antibody lacking an Fc portion, a single chain antibody and an antibody fragment consisting essentially of the antigen-binding domain.

6. The method of claim 1, wherein the monoclonal antibody is a recombinant antibody.

* * * * *